US011865411B2

(12) United States Patent
Bovell

(10) Patent No.: US 11,865,411 B2
(45) Date of Patent: Jan. 9, 2024

(54) PORTABLE SPORTS RACK AND DELIVERY SYSTEM

(71) Applicant: Gilbert M Bovell, Cherry Hill, NJ (US)

(72) Inventor: Gilbert M Bovell, Cherry Hill, NJ (US)

( * ) Notice: Subject to any disclaimer, the term of this patent is extended or adjusted under 35 U.S.C. 154(b) by 0 days.

(21) Appl. No.: 17/540,274

(22) Filed: Dec. 2, 2021

(65) Prior Publication Data

US 2022/0212063 A1 Jul. 7, 2022

Related U.S. Application Data

(60) Provisional application No. 63/270,060, filed on Oct. 21, 2021, provisional application No. 63/133,861, filed on Jan. 5, 2021.

(51) Int. Cl.

| A63B 69/00 | (2006.01) |
|---|---|
| A63B 47/00 | (2006.01) |
| A63B 71/02 | (2006.01) |
| A61L 2/16 | (2006.01) |
| A61L 2/26 | (2006.01) |
| A47B 81/00 | (2006.01) |

(52) U.S. Cl.
CPC ............ *A63B 47/002* (2013.01); *A47B 81/00* (2013.01); *A61L 2/16* (2013.01); *A61L 2/26* (2013.01); *A63B 69/0071* (2013.01); *A63B 71/023* (2013.01); *A61L 2202/15* (2013.01); *A63B 69/002* (2013.01); *A63B 69/0095* (2013.01); *A63B 2071/025* (2013.01); *A63B 2214/00* (2020.08); *A63B 2225/093* (2013.01); *A63B 2243/007* (2013.01); *A63B 2243/0025* (2013.01); *A63B 2243/0033* (2013.01)

(58) Field of Classification Search
CPC ............ A63B 47/002; A63B 2071/025; A63B 2225/093
USPC ......................................................... 473/422
See application file for complete search history.

(56) References Cited

U.S. PATENT DOCUMENTS

| 3,675,921 A * | 7/1972 | Meyers, Sr. ....... A63B 69/0071 473/448 |
|---|---|---|
| 4,610,373 A | 9/1986 | Sherbondy |
| 5,839,607 A | 11/1998 | Swanson |
| 6,663,119 B2 | 12/2003 | White |
| 7,997,594 B1 * | 8/2011 | Mortazavi ............... B62B 1/008 206/315.9 |

(Continued)

*Primary Examiner* — Mitra Aryanpour
(74) *Attorney, Agent, or Firm* — Ashok Tankha

(57) ABSTRACT

A portable sports rack and delivery system including an elongate rack enclosure, and a method of use thereof are provided. The elongate rack enclosure defines a storage space for accommodating balls stacked one above the other. A delivery opening, disposed at a first end of the elongate rack enclosure, receives, accommodates, and delivers an uppermost ball from the storage space. A base member, attached to a second end of the elongate rack enclosure, supports the stacked balls within the storage space. A release component including a compression spring, disposed on an upper surface of the base member, elastically compresses and expands to elevate and release the uppermost ball from the storage space for delivery through the delivery opening. A training component, operably and adjustably coupled to a rear section of the elongate rack enclosure, extends above the first end of the elongate rack enclosure to assist in training a sportsperson.

19 Claims, 33 Drawing Sheets

(56) References Cited

U.S. PATENT DOCUMENTS

| | | | |
|---|---|---|---|
| 8,900,074 B1* | 12/2014 | Johnson | A63B 63/00 |
| | | | 473/422 |
| 9,873,030 B2 | 1/2018 | Frostino | |
| 10,792,549 B2* | 10/2020 | Rivers | A63B 69/0071 |
| | | | 473/435 |
| 2006/0086631 A1 | 4/2006 | Williams | |
| 2007/0202969 A1 | 8/2007 | Girard | |
| 2011/0104004 A1 | 5/2011 | Bobbitt | |
| 2021/0069555 A1* | 3/2021 | Holliday, Jr. | A63B 47/002 |
| | | | 473/422 |
| 2022/0212063 A1* | 7/2022 | Bovell | A63B 69/0071 |
| | | | 473/422 |

* cited by examiner

PORTABLE SPORTS RACK AND DELIVERY SYSTEM

CROSS-REFERENCE TO RELATED APPLICATIONS

This application claims priority to and the benefit of the provisional patent application titled "Vertical Portable Basketball Rack and Deliver System", application No. 63/133,861, filed in the United States Patent and Trademark Office (USPTO) on Jan. 5, 2021, and the provisional patent application titled "Portable Sports Rack and Delivery System", application No. 63/270,060, filed in the USPTO on Oct. 21, 2021. The specifications of the above referenced patent applications are incorporated herein by reference in their entirety.

BACKGROUND

Sportspersons, for example, players, trainers, coaches, etc., generally have a need to store various sports equipment that are large or bulky, or have shapes that are difficult to store in a compact and organized manner. For example, ball-shaped sports equipment such as basketballs, volleyballs, footballs, etc., need to be stored in a manner where they are readily retrievable and prevented from rolling away on a sports court where a game is being played. Conventional sports bags provide limited and suboptimal space to store and carry sports equipment, for example, balls of different sports such as basketball, volleyball, soccer, football, etc. Some sports bags comprise a separate external pouch to carry a single ball. Most sportspersons typically need to store more than a single ball, which makes a sports bag that is designed to accommodate a single ball inappropriate. Moreover, it is generally cumbersome to remove a ball from these types of sports bags, for example, due to the fastening mechanisms that are used to secure the ball in the sports bag.

While some conventional sports racks allow storage of multiple balls therein, these sports racks are typically heavy cage-type structures that are configured for stationary or immovable storage. Due to their weight, structure, and difficulty in containing the balls stored therein, it is difficult to transport these sports racks, for example, move these sport racks on a sports court where a game is being played. Furthermore, most sports bags or sports racks store sports equipment horizontally as it is difficult to reach and retrieve the sports equipment, for example, balls, positioned towards the bottom of the sports bags or the sport racks when the sports bags or the sport racks are positioned in an upright position. Furthermore, a conventional sports rack is generally configured for storing sports equipment and not for facilitating the retrieval and use of the sports equipment stored in the sport rack on the sports court, for example, for allowing basketballs to be readily retrieved by a sportsperson practising on a basketball court, and for facilitating training of the sportsperson.

Hence, there is a long-felt need for a portable sports rack and delivery system and a method of use thereof for storing and transporting multiple sports equipment, for example, multiple balls of one or more sports such as basketball, volleyball, soccer, football, etc., in a compact and organized manner and in a substantially vertical position, while allowing convenient access to and ready retrieval of all balls stored therein, including the lowermost ball positioned at the bottom of a storage space defined therewithin. Furthermore, there is a need for a portable sports rack and delivery system and a method of use thereof for training sportspersons using the sports equipment stored therein and retrieved therefrom.

SUMMARY

This summary is provided to introduce a selection of concepts in a simplified form that are further disclosed in the detailed description. This summary is not intended to determine the scope of the claimed subject matter.

The system and the method disclosed herein address the above-recited need for a portable sports rack and delivery system and a method of use thereof for storing and transporting multiple sports equipment, for example, multiple balls of one or more sports such as basketball, volleyball, soccer, football, etc., in a compact and organized manner and in a substantially vertical position, while allowing convenient access to and ready retrieval of all balls stored therein, including the lowermost ball positioned at the bottom of a storage space defined therewithin. Furthermore, the portable sports rack and delivery system and the method of use thereof address the above-recited need for training sportspersons using the sports equipment stored therein and retrieved therefrom.

The portable sports rack and delivery system disclosed herein comprises an elongate rack enclosure, a delivery opening, a base member, a release component, and a training component. The elongate rack enclosure defines a storage space extending from a first end to a second end of the elongate rack enclosure. The storage space is configured to accommodate sports equipment comprising, for example, balls stacked substantially vertically, one above the other, and disposed in the storage space. The balls comprise, for example, basketballs, footballs, soccer balls, beachballs, handballs, etc. In an embodiment, the elongate rack enclosure is of a generally cylindrical shape and is configured to stand in a substantially vertical, upright position. The balls are stored in a substantially vertical orientation within the storage space of the elongate rack enclosure. The delivery opening is disposed at the first end of the elongate rack enclosure. The delivery opening is configured to receive, accommodate, and deliver an uppermost one of the stacked balls from the storage space of the elongate rack enclosure. In an embodiment, the portable sports rack and delivery system further comprises one or more stopper elements operably attached to the first end of the elongate rack enclosure. The stopper elements are configured to partially or fully cover the delivery opening and contain the uppermost ball within the storage space of the elongate rack enclosure.

The base member is attached to the second end of the elongate rack enclosure. The base member is configured to support the stacked balls within the storage space of the elongate rack enclosure. The release component is disposed on an upper surface of the base member within the storage space of the elongate rack enclosure. The release component is configured to elastically compress and expand to elevate and release the uppermost ball from the storage space of the elongate rack enclosure for delivery through the delivery opening. In an embodiment, the release component comprises a compression spring and a spring base. A first end of the compression spring is operably coupled to the base member. A second end of the compression spring is operably coupled to the spring base. The spring base, in operable communication with the compression spring, is configured to elevate the stacked balk remaining in the storage space of the elongate rack enclosure towards the delivery opening when the uppermost ball is removed from the storage space through the delivery opening. The release component disposed on the upper surface of the base member provides compression as the compression spring expands to elevate the balls and release the uppermost ball from the storage space for delivery through the delivery opening.

In an embodiment, the portable sports rack and delivery system further comprises a delivery system operably coupled to the release component. The delivery system comprises a guide element and a lever. The guide element defines a channel extending along a length of the elongate rack enclosure. The lever comprises a first end and a second end. The first end of the lever is connected to the release component. The second end of the lever extends outwardly from the channel of the guide element. The lever is configured to traverse the channel of the guide element and move the release component in an upward direction from the second end of the elongate rack enclosure towards the delivery opening at the first end of the elongate rack enclosure for delivering the uppermost ball from the storage space of the elongate rack enclosure. In an embodiment, the portable sports rack and delivery system further comprises a locking member attached to an end of the guide element proximal to the second end of the elongate rack enclosure. The locking member is configured to lock the lever, and in turn, the release component, in position at the end of the guide element.

The training component is operably and adjustably coupled to a rear section of the elongate rack enclosure. The training component is configured to extend above the first end of the elongate rack enclosure to assist in training a sportsperson. In an embodiment, the training component comprises a frame configured, for example, in a humanoid shape with a head, a body, and arms extending from the body. The arms are configured in a raised position to simulate an obstruction to a trajectory of a ball thrown by the sportsperson, for example, toward a basketball net, to assist in training the sportsperson. In an embodiment, the training component further comprises a mesh configured to cover spaces defined by the frame for optimally obstructing a ball thrown by the sportsperson to assist in training the sportsperson. In an embodiment, each of the arms of the training component is rotatably connected about a joint using a motorized control unit. The motorized control unit, when activated, is configured to rotate the arms of the training component and simulate an obstruction to a trajectory of a ball thrown by the sportsperson to assist in training the sportsperson. In another embodiment, the portable sports rack and delivery system further comprises a gear system operably coupled to and in engageable communication with a support member of the training component at the rear section of the elongate rack enclosure. The gear system, when activated, is configured to move the training component in any one of an upward direction, a downward direction, and lateral directions to simulate an obstruction to a trajectory of a ball thrown by the sportsperson to assist in training the sportsperson.

In an embodiment, the portable sports rack and delivery system further comprises a holder attached to the rear section of the elongate rack enclosure. The holder comprises a holding space and openings spaced at predetermined intervals thereon. The holder is configured to accommodate and secure the support member of the training component in the holding space at a required height by inserting a fastener through an opening of the support member and through one of the openings of the holder. The height of the training component is adjusted by sliding the support member in the holding space of the holder in an upward position or a downward position and securing the support member to one of the openings of the holder at a required height using the fastener. In another embodiment, the training component is adjustably coupled to the rear section of the elongate rack enclosure using a telescopic assembly.

In an embodiment, the portable sports rack and delivery system further comprises wheel assemblies, for example, casters, operably coupled to a bottom surface of the base member. The wheel assemblies are configured to transport the portable sports rack and delivery system. In an embodiment, the portable sports rack and delivery system further comprises a locking member operably coupled to each of at least two of the wheel assemblies. The locking member is configured to lock each of at least two wheel assemblies and brake the movement of the portable sports rack and delivery system. In an embodiment, the portable sports rack and delivery system further comprises a plate member, for example, a circular plate, attached to the bottom surface of the base member. The plate member is configured to stabilize the elongate rack enclosure and preclude the elongate rack enclosure from tipping when the elongate rack enclosure is in a substantially vertical, upright position.

In an embodiment, the portable sports rack and delivery system further comprises one or more handle elements attached to an outer surface of the elongate rack enclosure. The handle elements are configured to allow gripping and carrying of the portable sports rack and delivery system in a substantially horizontal position or a substantially vertical position. In an embodiment, the portable sports rack and delivery system further comprises an elongate opening disposed at a front section of the elongate rack enclosure. The elongate opening is configured to accommodate a display structure on the elongate rack enclosure. In an embodiment, the portable sports rack and delivery system further comprises multiple pockets of same and/or different shapes and sizes positioned at predetermined locations on an outer surface of the elongate rack enclosure. The pockets are configured to store items and accessories of the sports equipment.

In an embodiment, the portable sports rack and delivery system further comprises a sanitizing system operably coupled to the elongate rack enclosure. The sanitizing system comprises a reservoir and multiple nozzles. The reservoir is positioned in the rear section of the elongate rack enclosure. The reservoir is configured to contain a sanitizing solution for sanitizing one or more of the stacked balls in the storage space of the elongate rack enclosure. The nozzles are operably coupled to the reservoir and positioned at predetermined locations on the elongate rack enclosure. When activated, the nozzles, in fluid communication with the reservoir, are configured to dispense the sanitizing solution on one or more of the stacked balls in the storage space of the elongate rack enclosure.

In one or more embodiments, related systems comprise circuitry and/or programming for executing the methods disclosed herein. The circuitry and/or programming are of any combination of hardware, software, and/or firmware configured to execute the methods disclosed herein depending upon the design choices of a system designer. In an embodiment, various structural elements are employed depending on the design choices of the system designer.

DESCRIPTION OF THE DRAWINGS

The foregoing summary, as well as the following detailed description, is better understood when read in conjunction with the appended drawings. For illustrating the embodiments herein, exemplary constructions of the embodiments are shown in the drawings. However, the embodiments herein are not limited to the specific structures, components, and methods disclosed herein. The description of a structure or a component or a method step referenced by a numeral in a drawing is applicable to the description of that structure or component or method step shown by that same numeral in any subsequent drawing herein.

DETAILED DESCRIPTION

Figure 1:
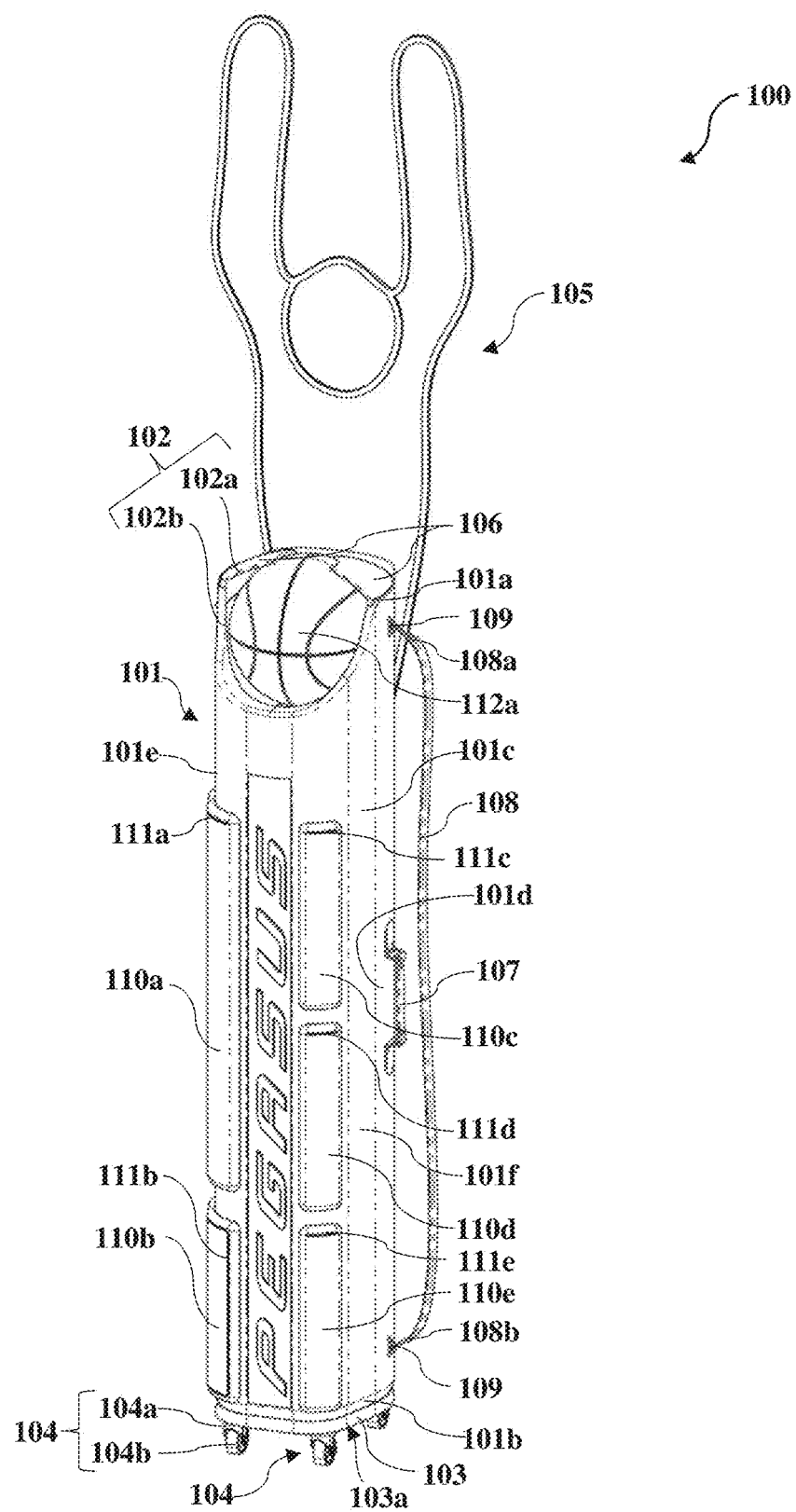
FIG. 1 exemplarily illustrates a front perspective view of an embodiment of a portable sports rack and delivery system.

FIG. 1 exemplarily illustrates a front perspective view of an embodiment of a portable sports rack and delivery system 100. The portable sports rack and delivery system 100 disclosed herein comprises an elongate rack enclosure 101, a delivery opening 102, a base member 103, a release component 115 exemplarily illustrated in FIGS. 2A-2B and FIGS. 7B-7C, and a training component 105. In an embodiment, the elongate rack enclosure 101 is of a generally cylindrical shape and is configured to stand in a substantially vertical, upright position as exemplarily illustrated in FIG. 1. In an embodiment, the elongate rack enclosure 101 is a hollow cylinder made of a durable, waterproof, outdoor fabric material, for example, nylon, ballistic nylon, corduroy, polyester, etc. Examples of materials used for manufacturing an internal structure of the elongate rack enclosure 101 are graphite, fiberglass, plastic, metal such as aluminum, etc. In an embodiment, the elongate rack enclosure 101 is a non-rigid, flexible, hollow, cylindrical structure adapted to accommodate sport equipment that is large or bulky, or have shapes that are difficult to store, for example, ball-shaped sports equipment. The elongate rack enclosure 101 is configured to be positioned in a substantially vertical, upright position as exemplarily illustrated in FIG. 1, during use and during transportation of the portable sports rack and delivery system 100. The height of the elongate rack enclosure 101 in the substantially vertical, upright position is, for example, between about 50 inches to about 55 inches. The width of the elongate rack enclosure 101 is, for example, between about 11 inches and about 14 inches.

Figure 2A:
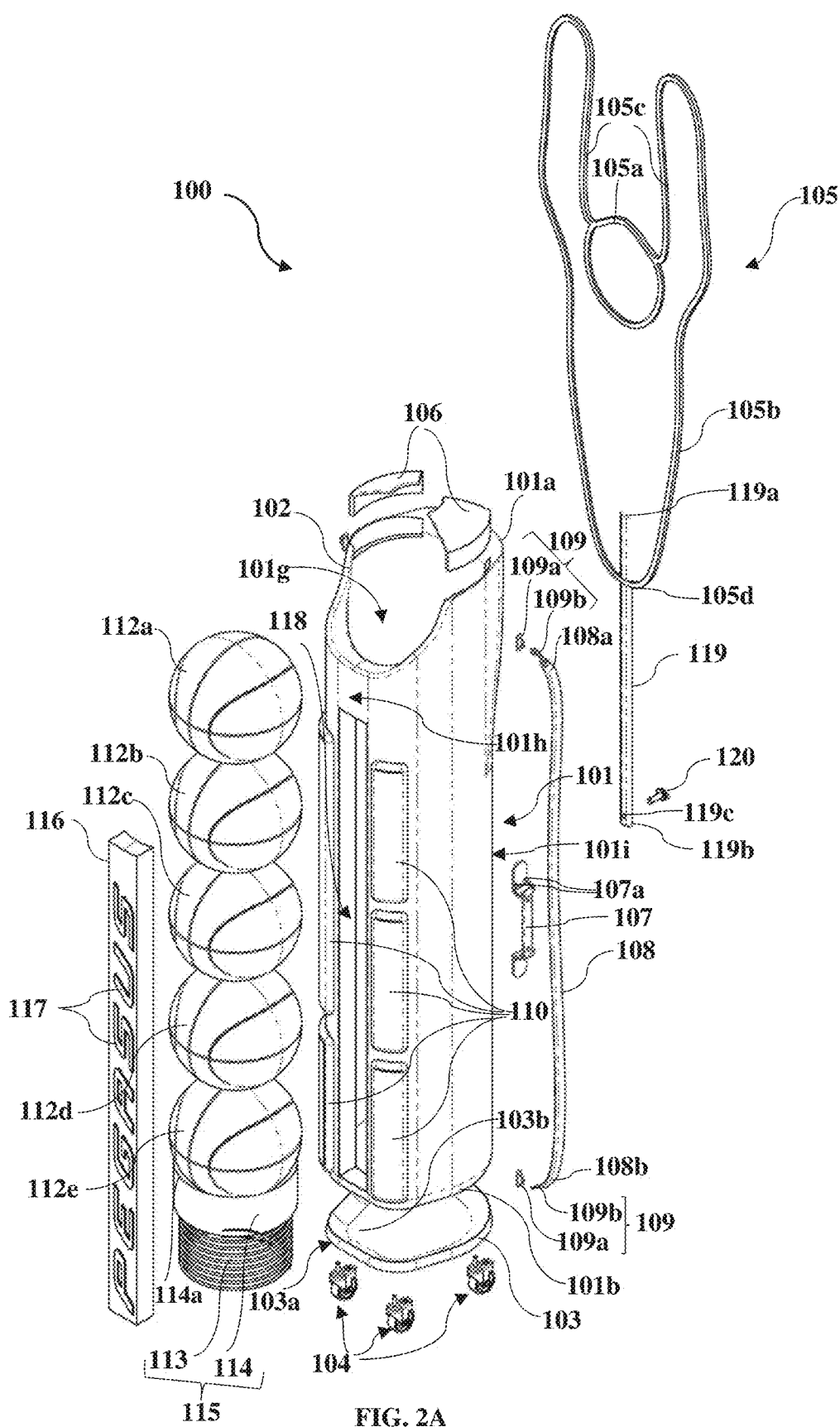
FIG. 2A exemplarily illustrates a front perspective, exploded view of an embodiment of the portable sports rack and delivery system.
Figure 2B:
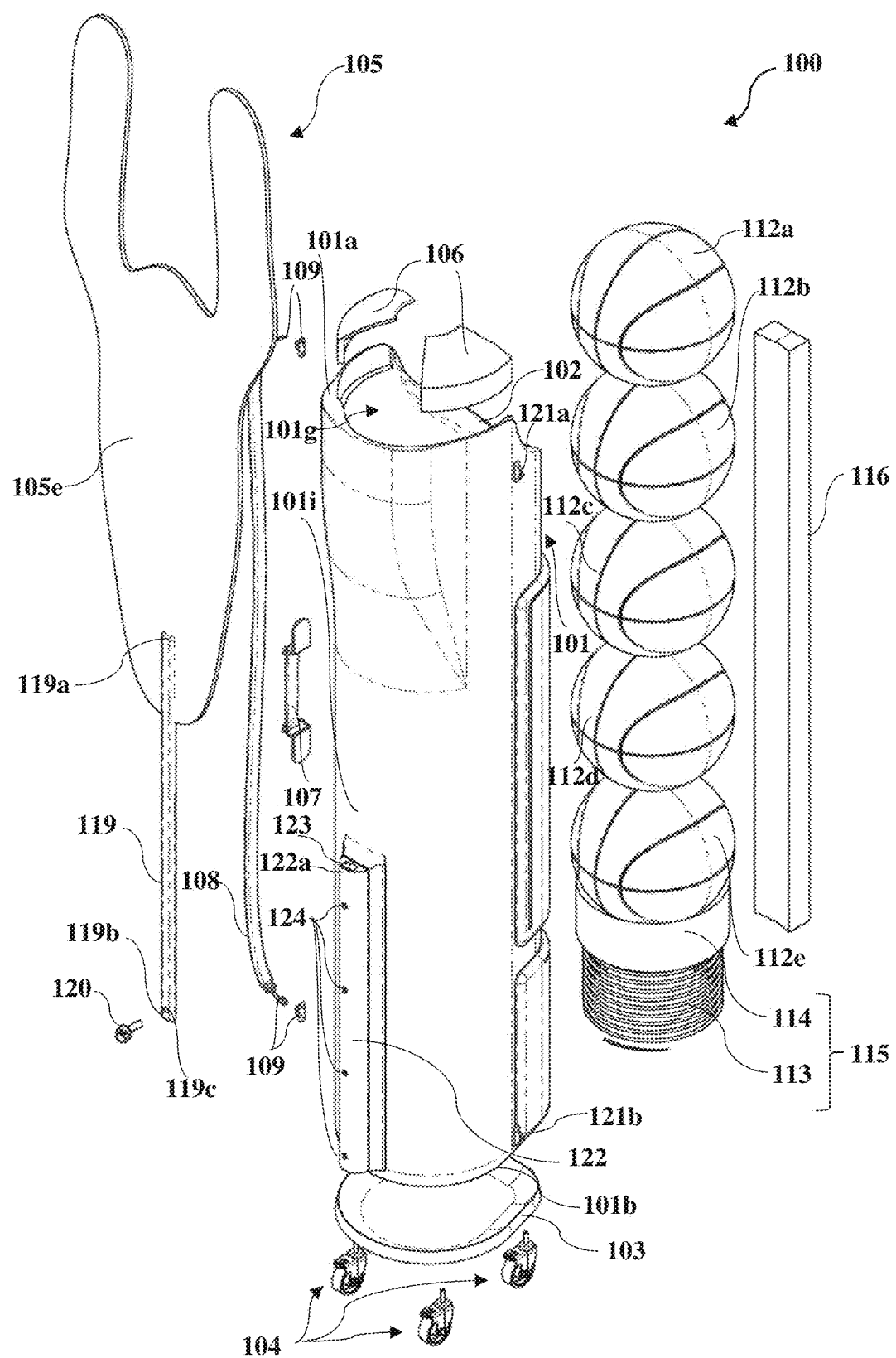
FIG. 2B exemplarily illustrates a rear perspective, exploded view of an embodiment of the portable sports rack and delivery system.
Figure 7A:
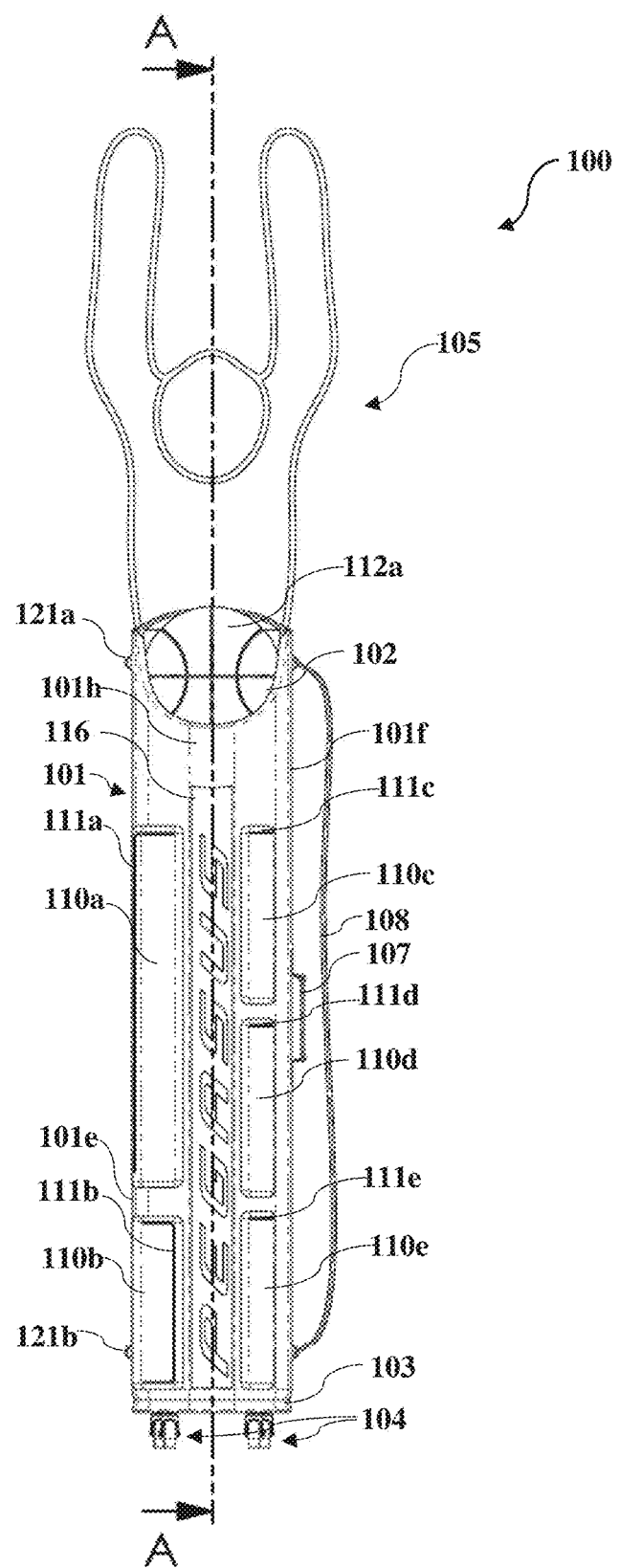
FIG. 7A exemplarily illustrates a front elevation view of the portable sports rack and delivery system shown in FIG. 1.
Figure 7B:
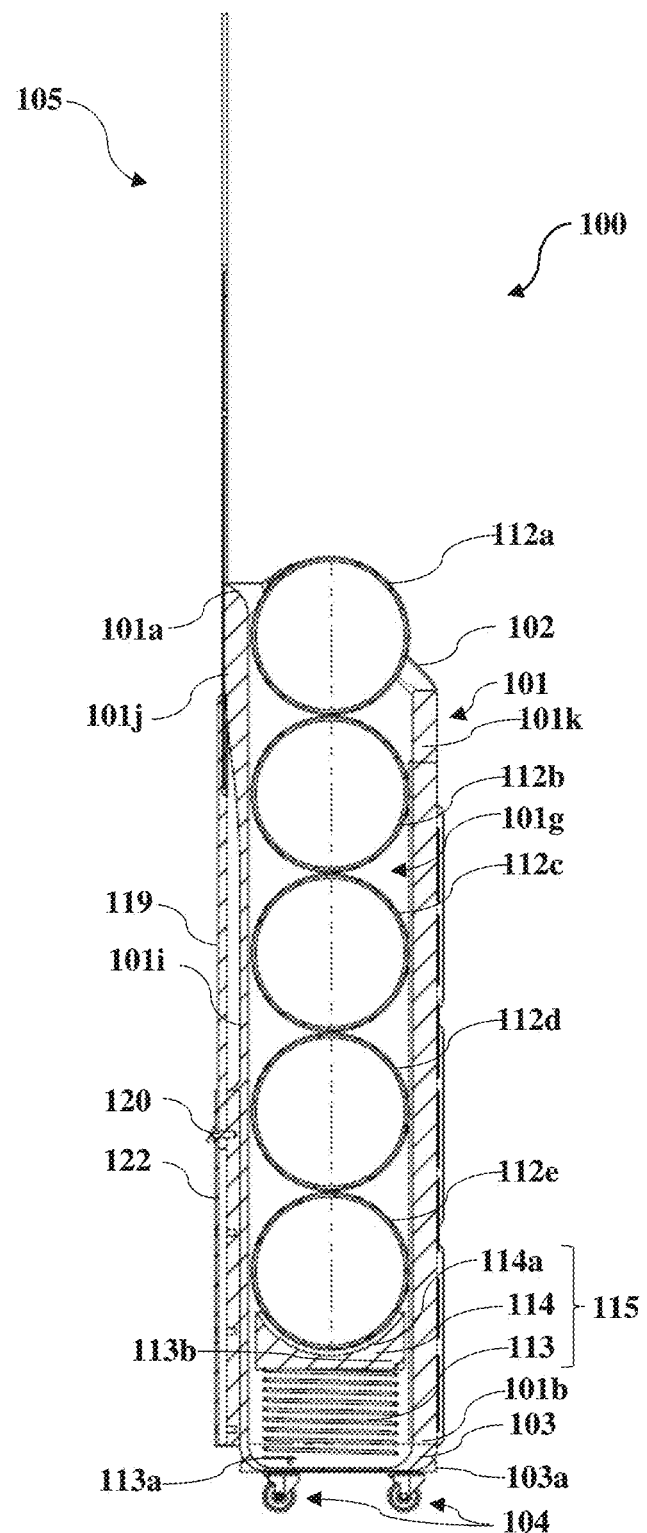
FIG. 7B exemplarily illustrates a cross-sectional view of the portable sports rack and deliver system taken along a section A-A shown in FIG. 7A.

The elongate rack enclosure 101 defines a storage space 101g exemplarily illustrated in FIGS. 2A-2B and FIG. 7B, extending from a first end, for example, an upper end 101a, to a second end, for example, a lower end 101b, of the elongate rack enclosure 101. In an embodiment, the upper end 101a of the elongate rack enclosure 101 is, for example, of a semi-circular shape, while the lower end 101b of the elongate rack enclosure 101 is, for example, of a curved square shape. The storage space 101g is configured to accommodate sports equipment comprising, for example, balls such as basketballs 112a, 112b, 112c, 112d, and 112e, stacked substantially vertically, one above the other, and disposed in the storage space 101g as exemplarily illustrated in FIGS. 2A-2B and FIG. 7B. The delivery opening 102 is disposed at the upper end 101a of the elongate rack enclosure 101. The delivery opening 102 is configured to receive, accommodate, and deliver an uppermost one of the stacked balls, for example, 112a, from the storage space 101g of the elongate rack enclosure 101. The delivery opening 102 delivers the uppermost ball 112a to a sportsperson, for example, a basketball player. In an embodiment, the delivery opening 102 is defined by two semicircles 102a and 102b in perpendicular relation to each other, where a first semicircle 102a is disposed in a horizontal direction at the upper end 101a of the elongate rack enclosure 101, and a second semicircle 102b is disposed in a vertical direction, perpendicular to the direction of the first semicircle 102a. In an example, the diameter of each of the semicircles 102a and 1021 is about 9.5 inches. The two semicircles 102a and 102b of the delivery opening 102 are configured to accommodate the uppermost ball 112a for delivery through the delivery opening 102. In an example, the height of the delivery opening 102 is about 6.5 inches.

In an embodiment, the portable sports rack and delivery system 100 further comprises one or more stopper elements 106 operably attached to the upper end 101a of the elongate rack enclosure 101. For example, two stopper elements 106 are operably attached to the upper end 101a of the elongate rack enclosure 101 as exemplarily illustrated in FIG. 1 and FIGS. 2A-2B. In an embodiment, the stopper elements 106 are operably attached to the upper end 101a of the elongate rack enclosure 101, for example, by any one of a snap-fit connection, a press fit connection, a lock mechanism, a fastening mechanism, glues, adhesives, etc. In an embodiment as exemplarily illustrated in FIG. 1, the stopper elements 106 are configured to partially cover the delivery opening 102 and contain the uppermost ball 112a within the storage space 101g of the elongate rack enclosure 101. In another embodiment (not shown), the stopper elements 106 are configured to fully cover the delivery opening 102 and contain the uppermost ball 112a within the storage space 101g of the elongate rack enclosure 101. Each of the stopper elements 106 is shaped, for example, as a partial truncated cone. The stopper elements 106 are made of a plastic material, for example, high-density polyethylene (HDPE).

The base member 103 is attached to the lower end 101b of the elongate rack enclosure 101. The base member 103 is configured to support the stacked balls, for example, basketballs 112a, 112b, 112c, 112d, and 112e exemplarily illustrated in FIGS. 2A-2B, within the storage space 101g of the elongate rack enclosure 101. In an embodiment, the base member 103 is configured as a counterweight base made, for example, of a metal alloy such as steel. In an embodiment, a bottom profile of the base member 103 is, for example, of a curved square shape, corresponding to the curved square shape of the lower end 101b of the elongate rack enclosure 101. In an embodiment, the base member 103 is attached to the lower end 101b of the elongate rack enclosure 101 using high-performance bonding materials, for example, epoxies, other glues, adhesives, etc. The thickness of the base member 103 is, for example, about 1.24 inches.

The release component 115 exemplarily illustrated in FIGS. 2A-2B and FIGS. 7B-7C, is disposed on the base member 103 as disclosed in the descriptions of FIGS. 2A-2B and FIG. 7B. The release component 115 vertically elevates the stacked balk, for example, basketballs 112b, 112c, 112d, and 112e to replace the uppermost ball 112a when the uppermost ball 112a is manually removed by a sportsperson. The training component 105 is operably and adjustably coupled to the elongate rack enclosure 101 as disclosed in the description of FIGS. 2A-2B. The training component 105 is configured to extend above the upper end 101a of the elongate rack enclosure 101 to assist in training a sportsperson. In an embodiment, the portable sports rack and delivery system 100 further comprises wheel assemblies, for example, casters 104, operably coupled to a bottom surface 103a of the base member 103. The casters 104 are configured to transport the portable sports rack and delivery system 100. The casters 104 support and provide mobility to the portable sports rack and delivery system 100 as disclosed in the description of FIG. 5. In an embodiment, the portable sports rack and delivery system 100 comprises four wear-resistant casters 104 as exemplarily illustrated in FIG. 10 and FIG. 11B.

In an embodiment, the portable sports rack and delivery system 100 further comprises one or more handle elements, for example, 107 and 108, attached to an outer surface 101c of the elongate rack enclosure 101. The handle elements, for example, 107 and 108, are configured to allow gripping and carrying of the portable sports rack and delivery system 100 in a substantially horizontal position or a substantially vertical position. In an embodiment, one of the handle elements is configured as a bag handle 107 of a small size configured to allow a user, for example, a sportsperson, to grip the portable sports rack and delivery system 100 in a single hand. The bag handle 107 is, for example, of a half-square shape and is disposed, for example, at a central location 101d on a right side 101f of the elongate rack enclosure 101. In an embodiment, the hag handle 107 is made of a fabric material, for example, nylon. In another embodiment, the bag handle 107 is made of a rigid material, for example, metal, wood, other materials used for manufacturing handles, and any combination thereof. In an example, the length of the bag handle 107 is about 6 inches. For carrying the portable sports rack and delivery system 100 using the bag handle 107, the user grips the bag handle 107 and orients the portable sports rack and delivery system 100 in a substantially horizontal position. The bag handle 107 allows the portable sports rack and delivery system 100 to be carried and transported in a substantially horizontal position.

In an embodiment, the other one of the handle elements is configured as an elongate strap 108, for example, a bag strap or a duffel strap, made of a fabric material, for example, nylon. In an example, the length of the elongate strap 108 is about 49 inches. The elongate strap 108 is attached to the elongate rack enclosure 101, for example, by connecting opposing ends 108a and 108b of the elongate strap 108 proximal to the upper end 101a and the lower end 101b of the elongate rack enclosure 101 respectively, using connector elements 109. A user, for example, a sportsperson, uses the elongate strap 108 as a shoulder strap to carry the portable sports rack and delivery system 100 in a substantially vertical, upright position. For carrying the portable sports rack and delivery system 100 oriented in a substantially vertical, upright position using the elongate strap 108, the user positions the elongate strap 108 on the user's shoulder and lifts or carries the portable sports rack and delivery system 100. The elongate strap 108, therefore, allows the portable sports rack and delivery system 100 to be carried and transported in a substantially vertical, upright position. Through the use of the handle elements 107 and 108, the portable sports rack and delivery system 100 allows convenient transport of sports equipment, for example, multiple basketballs 112a, 112b, 112c, 112d, and 112e stored therewithin.

In an embodiment, the portable sports rack and delivery system 100 further comprises multiple pockets 110a, 110b, 110c, 110d, and 110e of same and/or different shapes and sizes disposed at predetermined locations on the outer surface 101c of the elongate rack enclosure 101. For example, an elongate pocket 110a and a small-sized pocket 110b are disposed on a left side 101e of the elongate rack enclosure 101, while pockets 110c, 110d, and 110e are disposed on a right side 101f of the elongate rack enclosure 101 as exemplarily illustrated in FIG. 1. In an embodiment, each of the pockets 110a, 110b, 110c, 110d, and 110e is configured in a generally rectangular shape. In an example, the lengths of the pockets 110a and 110b on the left side 101e of the elongate rack enclosure 101 are about 25 inches and 12 inches respectively, while the width of each of the pockets 110a and 110b is about 15 inches. In an example, the length of each of the pockets 110e, 110d, and 110e on the right side 101f of the elongate rack enclosure 101 is about 12.5 inches, while the width of each of the pockets 110c, 110d, and 110e is about 3.5 inches. The pockets 110a, 110b, 110e, 110d, and 110e are configured to store items and accessories of the sports equipment. The same or differently-sized and shaped pockets 110a, 110b, 110c, 110d, and 110e accommodate items and accessories of the sports equipment of different shapes and sizes, for example, gloves, elbow pads, sports apparel, sports gear, sports footwear, etc. In an embodiment, the pockets 110a, 110b, 110c, 110d, and 110e are made of a durable, waterproof, outdoor fabric material, for example, nylon. In an embodiment, the pockets 110a, 110b, 110c, 110d, and 110e comprise zippers 111a, 111b, 111c, 111d, and 111e respectively, for securing the items and the accessories of the sports equipment accommodated in the pockets 110a, 110b, 110e, 110d, and 110e. The zippers 111a, 111b, 111c, 111d, and 111e bind the edges of openings configured in the pockets 110a, 111b, 110c, 110d, and 110e respectively, for securing the items and the accessories of the sports equipment accommodated therewithin. In an example, the overall height of the portable sports rack and delivery system 100 ranges from about 50 inches to about 70 inches, and the overall width of the portable sports rack and delivery system 100 ranges from about 10 inches to about 13 inches.

FIG. 2A exemplarily illustrates a front perspective, exploded view of an embodiment of the portable sports rack and delivery system 100. The exploded view in FIG. 2A exemplarily illustrates the elongate rack enclosure 101 with the delivery opening 102, the base member 103, the wheel assemblies 104, the training component 105, the stopper elements 106, the handle elements 107 and 108, and the pockets 110 of the portable sports rack and delivery system 100. As exemplarily illustrated in FIG. 2A, the elongate rack enclosure 101 is of a generally cylindrical shape and is configured to stand unsupported in a substantially vertical, upright position. In an embodiment, the storage space 101g of the elongate rack enclosure 101 accommodates multiple balls, for example, five basketballs 112a, 112b, 112c, 112d, and 112e, within the elongate rack enclosure 101 as exemplarily illustrated in FIG. 7B. The diameters of the basketballs 112a, 112b, 112c, 112d, and 112e are, for example, about 27 inches to about 30 inches. For example, the storage space 101g of the elongate rack enclosure 101 accommodates 27.5-inch, or 28.5-inch, or 29.5-inch basketballs made of thermoplastic polyurethane (TPU). For purposes of illustration, the disclosure herein refers to the balls being basketballs 112a, 112b, 112c, 112d, and 112e accommodated substantially vertically, one above the other within the storage space 101g of the elongate rack enclosure 101; however, the scope of the portable sports rack and delivery system 100 is not limited to accommodating only basketballs 112a, 112b, 112c, 112d, and 112e, but may be extended to include other ball-shaped sports equipment, for example, footballs, soccer balls, volleyballs, beachballs, handballs, etc. In an embodiment, the portable sports rack and delivery system 100 is configured as a portable, vertical, basketball rack system or a portable basketball equipment bag for holding, transporting, and using basketballs 112a, 112b, 112c, 112d, and 112e for practice and drills by all levels of basketball players and coaches. As exemplarily illustrated in FIGS. 2A-2B, the basketballs 112a, 112b, 112c, 112d, and 112e are stacked substantially vertically, one above the other, and stored in a substantially vertical orientation within the storage space 101g of the elongate rack enclosure 101.

In an embodiment, the portable sports rack and delivery system 100 further comprises an elongate opening 118 disposed at a front section 101h of the elongate rack enclosure 101. The elongate opening 118 is configured to accommodate a display structure 116 on the elongate rack enclosure 101. The elongate opening 118 is, for example, of a rectangular shape, and accommodates a rectangular-shaped display structure 116 as exemplarily illustrated in FIGS. 2A-2B. In an example, the length of the display structure 116 is about 42 inches, and the width of the display structure 116 is about 3 inches. The display structure 116 is made of a transparent material, for example, clear polypropylene (PP), clear polyethylene (PE), etc., that provides a window to see therethrough into the storage space 101g of the elongate rack enclosure 101. In an embodiment, the display structure 116 is configured to display media content, for example, logos 117, product names, images, marketing material, advertising indicia, etc. In an embodiment, the logos 117 attached on the display structure 116 are made of a plastic material, for example, high-density polyethylene (HDPE).

The handle elements 107 and 108 are attached to the outer surface 101c of the elongate rack enclosure 101. In an embodiment, the bag handle 107 is attached to the central location 101d on the right side 101f of the elongate rack enclosure 101 exemplarily illustrated in FIG. 1, using a fastening material, for example, an epoxy. In another embodiment, the bag handle 107 is attached to the central location 101d of the elongate rack enclosure 101 using fasteners, for example, screws, bolts, etc., inserted through openings 107a configured on the bag handle 107. In an embodiment, the opposing ends 108a and 108b of the elongate strap 108 are attached proximal to the upper end 101a and the lower end 101b of the elongate rack enclosure 101 respectively, using the connector elements 109. In an embodiment, each of the connector elements 109 comprises mating connectors 109a and 109b configured to connect the opposing ends 108a and 108b of the elongate strap 108 proximal to the upper end 101a and the lower end 101b of the elongate rack enclosure 101. For example, the mating connectors comprise snap hooks 109b such as lobster hooks or bolt snaps connected to the opposing ends 108a and 108b of the elongate strap 108, and corresponding ring-shaped connectors 109a attached proximal to the upper end 101 and the lower end 101b of the elongate rack enclosure 101. The snap hooks 109b connect to or hook onto the ring-shaped connectors 109a to attach the opposing ends 108a and 108b of the elongate strap 108 proximal to the upper end 101a and the lower end 101b of the elongate rack enclosure 101. In an example, the connector elements 109 are made of steel.

The release component 115 of the portable sports rack and delivery system 100 exemplarily illustrated in FIGS. 2A-2B, is disposed on an upper surface 103b of the base member 103, within the storage space 101g of the elongate rack enclosure 101. The release component 115 is configured to elastically compress and expand to elevate and release the uppermost ball, for example, the uppermost basketball 112a, from the storage space 101g of the elongate rack enclosure 101 for delivery through the delivery opening 102. In an embodiment, the release component 115 comprises a compression spring 113 and a spring base 114. The length of the compression spring 113 when loaded with five basketballs 112a, 112b, 112c, 112d, and 112e as exemplarily illustrated in FIGS. 2A-2B and FIG. 7B, is, for example, about 6 inches. The compression spring 113 is made, for example, of a metal alloy such as steel. In an embodiment, the spring base 114 is a generally cylindrical structure comprising a curved upper surface 114a configured to accommodate curved surfaces of ball-shaped sports equipment. For example, the curved upper surface 114a of the spring base 114 accommodates the lowermost basketball 112e in the storage space 101g of the elongate rack enclosure 101. The spring base 114 is made of a plastic material, for example, high-density polyethylene (HDPE). The spring base 114, in operable communication with the compression spring 113, is configured to elevate the stacked balls, for example, the stacked basketballs 112b, 112c, 112d, and 112e remaining in the storage space 101g of the elongate rack enclosure 101 towards the delivery opening 102, when the uppermost ball 112a is removed from the storage space 101g through the delivery opening 102 by a sportsperson as disclosed in the description of FIG. 7B.

The portable sports rack and delivery system 100 holds the stacked basketballs 112a, 112b, 112c, 112d, and 112e substantially vertically, one above the other, with lift resistance at the base member 103 via the release component 115. When compressed, the compression spring 113 at the base member 103 provides lift resistance to the stacked basketballs 112a, 112b, 112c, 112d, and 112e disposed thereon via the spring base 114. When the uppermost basketball 112a is removed from the storage space 101g through the delivery opening 102 of the elongate rack enclosure 101 by a sportsperson, the compression spring 113 expands and, via the spring base 114, vertically elevates the stacked basketballs 112b, 112c, 112d, and 112e remaining in the storage space 101g of the elongate rack enclosure 101 towards the delivery opening 102. The compression spring 113 expands to elevate the spring base 114 to a predetermined height, and in turn, to elevate the remaining basketballs 112b, 112c, 112d, and 112e such that the next uppermost basketball 112b is positioned to be released from the storage space 101g of the elongate rack enclosure 101 for delivery through the delivery opening 102. The predetermined height to which the compression spring 113 expands within the storage space 101g of the elongate rack enclosure 101 to elevate the remaining basketballs 112b, 112c, 112d, and 112e is, for example, about 40 inches to about 45 inches.

The training component 105 is operably and adjustably coupled to a rear section 101i of the elongate rack enclosure 101. In an embodiment, the training component 105 is operably coupled to the rear section 101i of the elongate rack enclosure 101 via a support member 119. The parts 105a, 105b, and 105c of the training component 105 are disclosed in the description of FIG. 3. In an embodiment, the training component 105 comprises a flat solid rear surface 105e as exemplarily illustrated in FIG. 2B. The flat solid rear surface 105e of the training component 105 blocks an object, for example, a basketball, thrown at the training component 105 by a sportsperson during training of the sportsperson. In an embodiment, the support member 119 is configured, for example, as a stick-like or a rod-like structure. Examples of materials used for manufacturing the support member 119 are wood, steel, aluminum, fiber glass, plastic, etc. An upper end 119a of the support member 119 is attached to the flat solid rear surface 105e of the training component 105, proximal to the lower end 105d of the training component 105. An opening 119c is configured at a distal lower end 119b of the support member 119 for facilitating connection of the support member 119 to the rear section 101i of the elongate rack enclosure 101.

The support member 119 is connected to the rear section 101i of the elongate rack enclosure 101, for example, by inserting a fastener, for example, a lock pin 120, into the opening 119c of the support member 119 and into one of the openings 124 configured at the rear section 101i of the elongate rack enclosure 101 as exemplarily illustrated in FIG. 2B, FIGS. 6A-6B, FIGS. 7B-7C. The lock pin 120 is made, for example, of a metal alloy such as steel. In an example, the length of the lock pin 120 is about 1.2 inches. In an embodiment, the lock pin 120 is configured as an adjustable push-in button, for example, made of steel, for adjustably connecting the support member 119 of the training component 105 to the rear section 101i of the elongate rack enclosure 101. The training component 105 extends above the upper end 101a of the elongate rack enclosure 101 to assist in training a sportsperson as disclosed in the description of FIG. 3. In a prophetic embodiment, the portable sports rack and delivery system 100 is collapsible for convenient storage, when the training component 105 is removed and the portable sports rack and delivery system 100 is not in use for storing the sports equipment, for example, the basketballs 112a, 112b, 112c, 112d, and 112e.

FIG. 2B exemplarily illustrates a rear perspective, exploded view of an embodiment of the portable sports rack and delivery system 100. In an embodiment, the portable sports rack and delivery system 100 further comprises a holder 122 attached to the rear section 101i of the elongate rack enclosure 101 as exemplarily illustrated in FIG. 28. The holder 122 is configured to accommodate and secure the support member 119 of the training component 105 using a fastener, for example, a lock pin 120, as disclosed in the description of FIG. 7C. The holder 122 receives the distal lower end 119b of the support member 119 through a receptacle 123 configured at an upper end 122a of the holder 122. Examples of materials used for manufacturing the holder 122 are plastics, metals, etc. The length of the holder 122 is, for example, about 22 inches. In an embodiment, the holder 122 comprises openings 124 spaced at predetermined intervals thereon. In an example, the openings 124 of the holder 122 are equally spaced about 6 inches apart from each other. In an embodiment, the openings 124 are positioned along a length of the holder 122. The diameter of each of the openings 124 is, for example, about 0.39 inches. The holder 122 is configured to accommodate and secure the support member 119 of the training component 105 at a required height by inserting the fastener, for example, the lock pin 120, through the opening 119c of the support member 119 exemplarily illustrated in FIGS. 2A-3, and through one of the openings 124 of the holder 122 as disclosed in the description of FIG. 7C.

Figure 3:
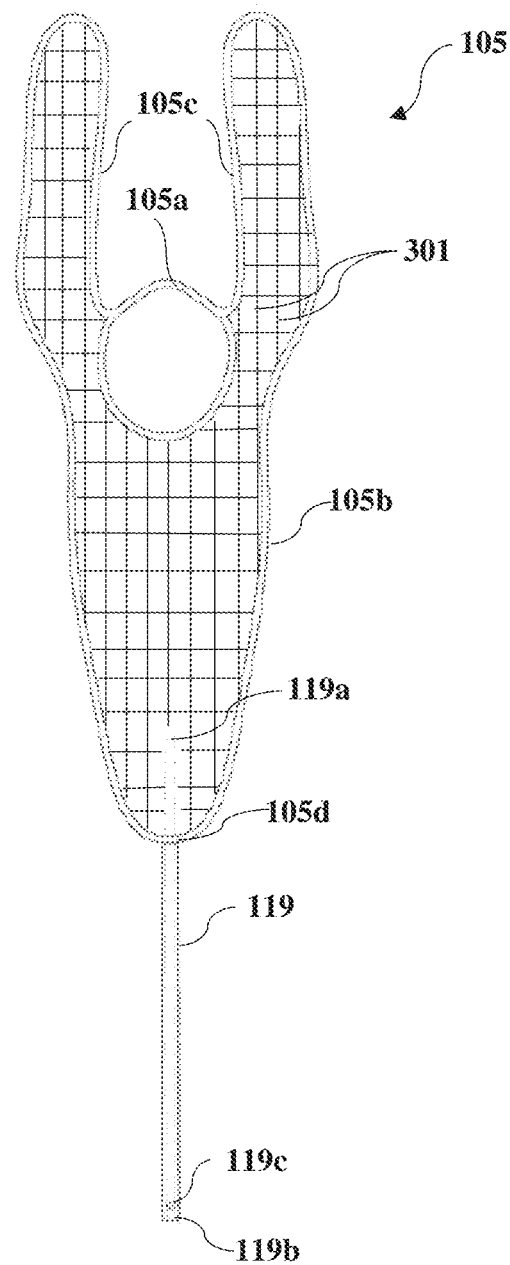
FIG. 3 exemplarily illustrates a front elevation view of a training component of an embodiment of the portable sports rack and delivery system.

FIG. 3 exemplarily illustrates a front elevation view of the training component 105 of an embodiment of the portable sports rack and delivery system 100. In an embodiment as exemplarily illustrated in FIG. 3, the training component 105 comprises a frame configured, for example, in a humanoid shape with a head 105a, a body 105b, and arms 105c extending from the body 105b. In an embodiment, the frame defining the head 105a, the body 105b, and the arms 105c of a humanoid is a wire frame. In an embodiment, the frame comprises the flat solid rear surface 105e as exemplarily illustrated in FIG. 2B and as disclosed in the description of FIG. 2A. The arms 105c are configured in a raised position to simulate an obstruction to a trajectory of a ball thrown by a sportsperson, for example, toward a basketball net, to assist in training the sportsperson. The frame of the training component 105 is made, for example, from plastic, or a metal such as aluminum, etc. The length of the frame comprising the head 105a, the body 105b, and the extended arms 105c is, for example, about 47 inches. In an embodiment, the frame comprising the head 105a, the body 105b, and the extended arms 105c is foldable for convenient storage.

In an embodiment, the training component 105 further comprises a mesh 301 configured to cover spaces defined by the frame comprising the head 105a, the body 105b, and the arms 105c for optimally obstructing the ball thrown by the sportsperson to assist in training the sportsperson. The mesh 301 is made of a fabric material, for example, nylon, polyester, etc. FIG. 3 also illustrates the support member 119 extending from a lower end 105d of the training component 105. The length of the support member 119 is, for example, about 27 inches. The width of the support member 119 is, for example, about 1 inch. In an embodiment, the support member 119 is a generally cylindrical structure. In an example, the diameter of the support member 119 is about 0.5 inches. In an embodiment, an upper end 119a of the support member 119 extends into the mesh 301 of the training component 105 as exemplarily illustrated in FIG. 3. The portion of the support member 119 extending into the mesh 301 is, for example, about 20 inches. The support member 119 extends downwardly from the training component 105 and is adjustably connected to the rear section 101i of the elongate rack enclosure 101, for example, using a fastener, for example, a lock pin 120 exemplarily illustrated in FIGS. 2A-2B, inserted into the opening 119c positioned at the lower end 119b of the support member 119. The diameter of the opening 119c is, for example, about 0.4 inches.

The training component 105 extending upwardly from the support member 119 is configured to serve as a practice defender to provide a hands-up defense for training the sportsperson, for example, a basketball player, during practices and drills. The training component 105 provides an obstruction to the ball thrown by the sportsperson. During practices and drills, the basketball player can shoot or pass over or around the training component 105 for simulating real-time game situations. The training component 105 assists sportspersons, for example, basketball players, to practice their arcs, practice breaking around players, and improving their floaters. The training component 105 aids sportspersons in visualizing the opposition for practicing independently.

Figure 4:
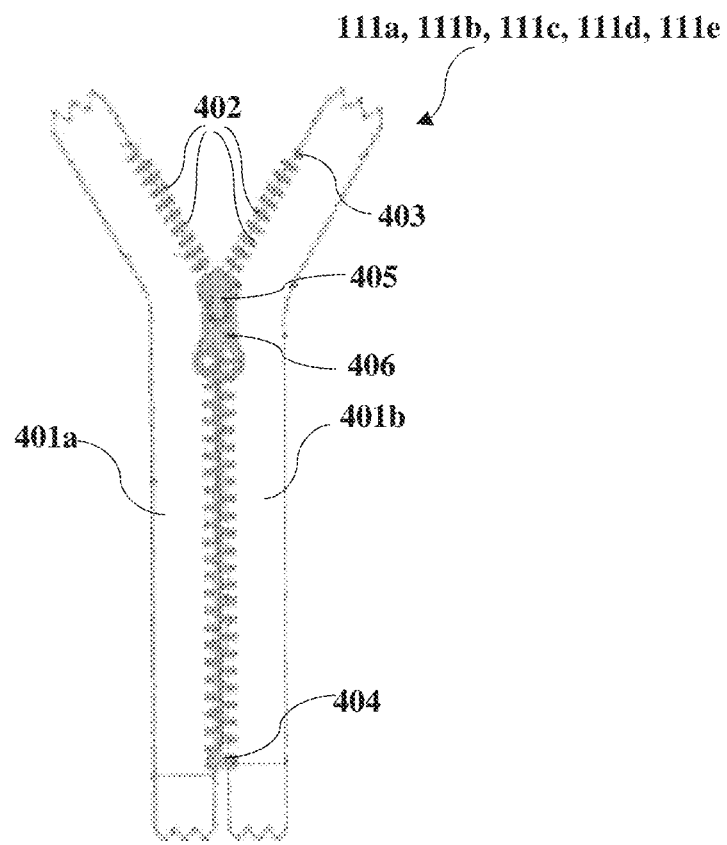
FIG. 4 exemplarily illustrates a front elevation view of a fastening element configured to fasten each of multiple pockets of an embodiment of the portable sports rack and delivery system.

FIG. 4 exemplarily illustrates a front elevation view of a fastening element configured to fasten each of multiple pockets 110a, 110b, 110c, 110d, and 110e of an embodiment of the portable sports rack and delivery system 100 shown in FIG. 1. In an embodiment, the fastening element is a zipper 111a, 111b, 111c, 111d, 111e configured to fasten each pocket 110a, 110b, 110c, 110d, 110e respectively, for securing the items and the accessories of the sports equipment accommodated therewithin. In an embodiment, each zipper 111a, 111b, 111c, 111d, 111e comprises two tapes 401a and 401b, two rows of protruding teeth 402, and a slider 405 with a pull tab 406. The two tapes 401a and 401b are made, for example, from polyester, synthetic fiber, vinyl, cotton, etc. The two rows of protruding teeth 402 originate from a lower stop 404. The lower stop 404 connects the two tapes 401a and 401b to each other. One row of the protruding teeth 402 terminates at an upper stop 403. The protruding teeth 402 are made, for example, from plastic or metal. The two rows of protruding teeth 402 are configured to interdigitate or link with each other. The slider 405, operated by hand using the pull tab 406, moves along the rows of protruding teeth 402. Inside the slider 405 is a Y-shaped channel that meshes together or separates the opposing rows of protruding teeth 402, depending on the direction of movement of the slider 405. When the slider 405 moves in the upward direction, the slider 405 meshes together the opposing rows of protruding teeth 402 and terminates at the upper stop 403, thereby closing the zipper 111a, 111b, 111c, 111d, 111e for securing the items and the accessories of the sports equipment accommodated within the pocket 110a, 110b, 110c, 110d, 110e. When the slider 405 moves in the downward direction, the slider 405 separates the opposing rows of protruding teeth 402 and terminates at the lower stop 404, thereby opening the zipper 111a, 111b, 111c, 111d, 111e and providing access to the items and the accessories of the sports equipment accommodated within the pocket 110a, 110b, 110c, 110d, 110e.

Figure 5:
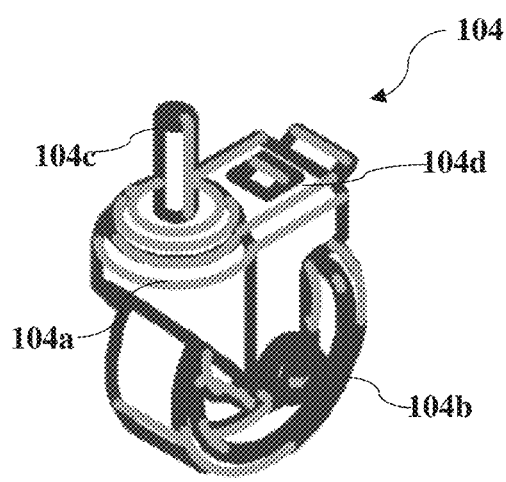
FIG. 5 exemplarily illustrates a perspective view of one of multiple wheel assemblies configured to transport an embodiment of the portable sports rack and delivery system.

FIG. 5 exemplarily illustrates a perspective view of one of multiple wheel assemblies, for example, the casters 104, configured to transport an embodiment of the portable sports rack and delivery system 100 shown in FIG. 1. In an embodiment, the portable sports rack and delivery system 100 comprises four casters 104 operably coupled to the bottom surface 103a of the base member 103 as exemplarily illustrated in FIG. 1, FIG. 10, and FIG. 11B, for transporting the portable sports rack and delivery system 100. The casters 104 are, for example, swivel casters, configured to turn the wheels 104b and move the portable sports rack and delivery system 100 in any direction. Each of the casters 104 comprises a mount 104a and a wheel 104b. The mount 104a is configured to mount the wheel 104b to the bottom surface 103a of the base member 103. The height of the mount 104a is, for example, about 1.5 inches. The diameter of the wheel 104b is, for example, about 2 inches. In an embodiment, the mount 104a comprises a stem 104c configured to attach the mount 104a, and in turn, the wheel 104b, to the bottom surface 103a of the base member 103. The stem 104c protrudes upwardly from the mount 104a for attaching each caster 104 to the bottom surface 103a of the base member 103. In another embodiment (not shown), a stemless caster is used for which a bolt is used to attach the stemless caster to the bottom surface 103a of the base member 103. In another embodiment shown), the mount 104a is a plate-type mount comprising bolt holes through which bolts are inserted to connect the mount 104a to the bottom surface 103a of the base member 103.

In an embodiment, the portable sports rack and delivery system 100 further comprises a locking member 104d operably coupled to each of at least two of the casters 104. In an embodiment, the locking member 104d is operably coupled to all of the casters 104 as exemplarily illustrated in FIGS. 2A-2B, FIG. 10, and FIG. 11B. The locking member 104d is configured to lock the wheel 104b of each of the casters 104 and brake the movement of the portable sports rack and delivery system 100. The locking member 104d is configured as a lock or a brake to preclude rolling of the wheels 104b when the portable sports rack and delivery system 100 is in place. The casters 104 are made, for example, of a plastic material, for example, high-density polyethylene (HDPE). In another example, the casters 104 are made of metal. The material, wheel diameter, tread width, load rating, and overall height of the casters 104 are configurable to provide optimal mobility to the portable sports rack and delivery system 100 in different environments.

Figure 6A:
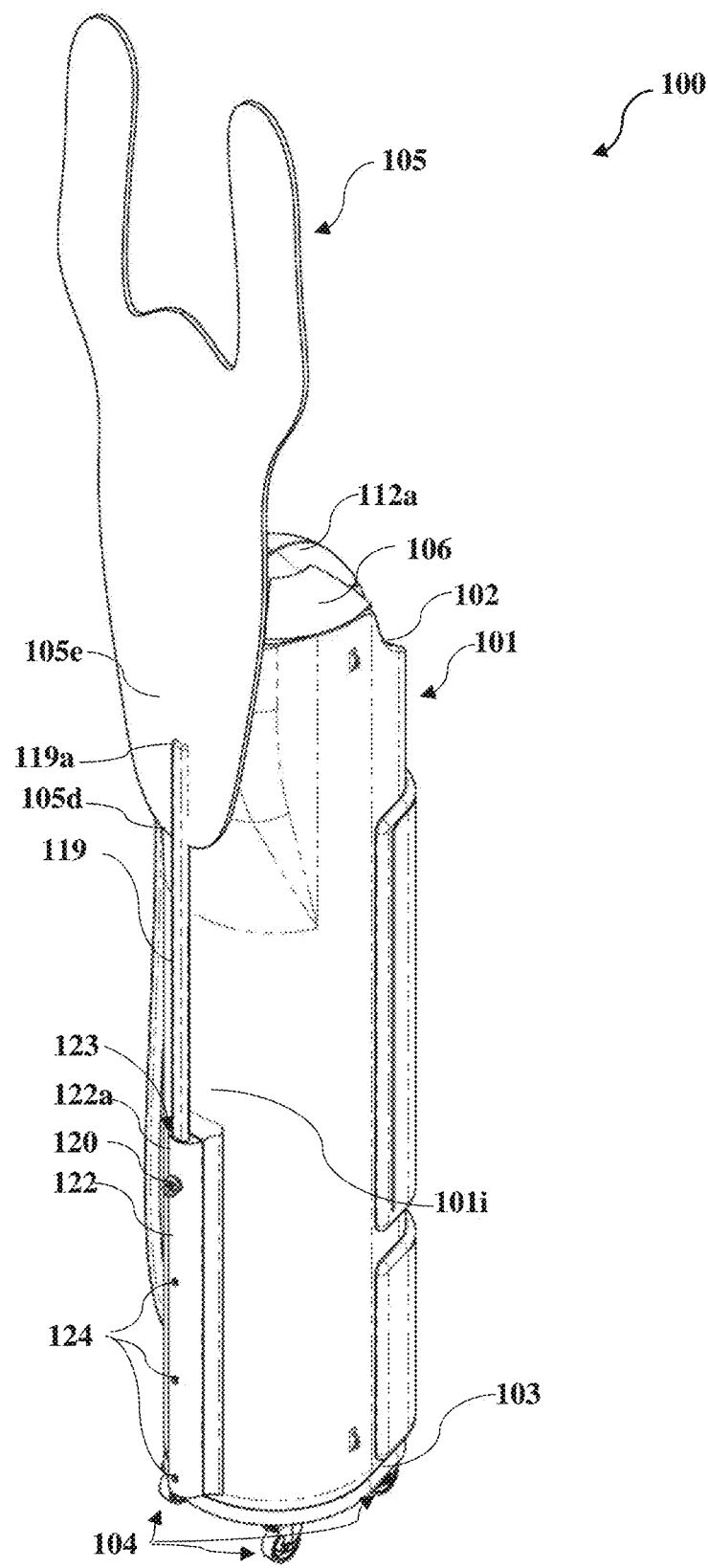
FIG. 6A exemplarily illustrates a rear perspective view of the portable sports rack and delivery system shown in FIG. 1.
Figure 6B:
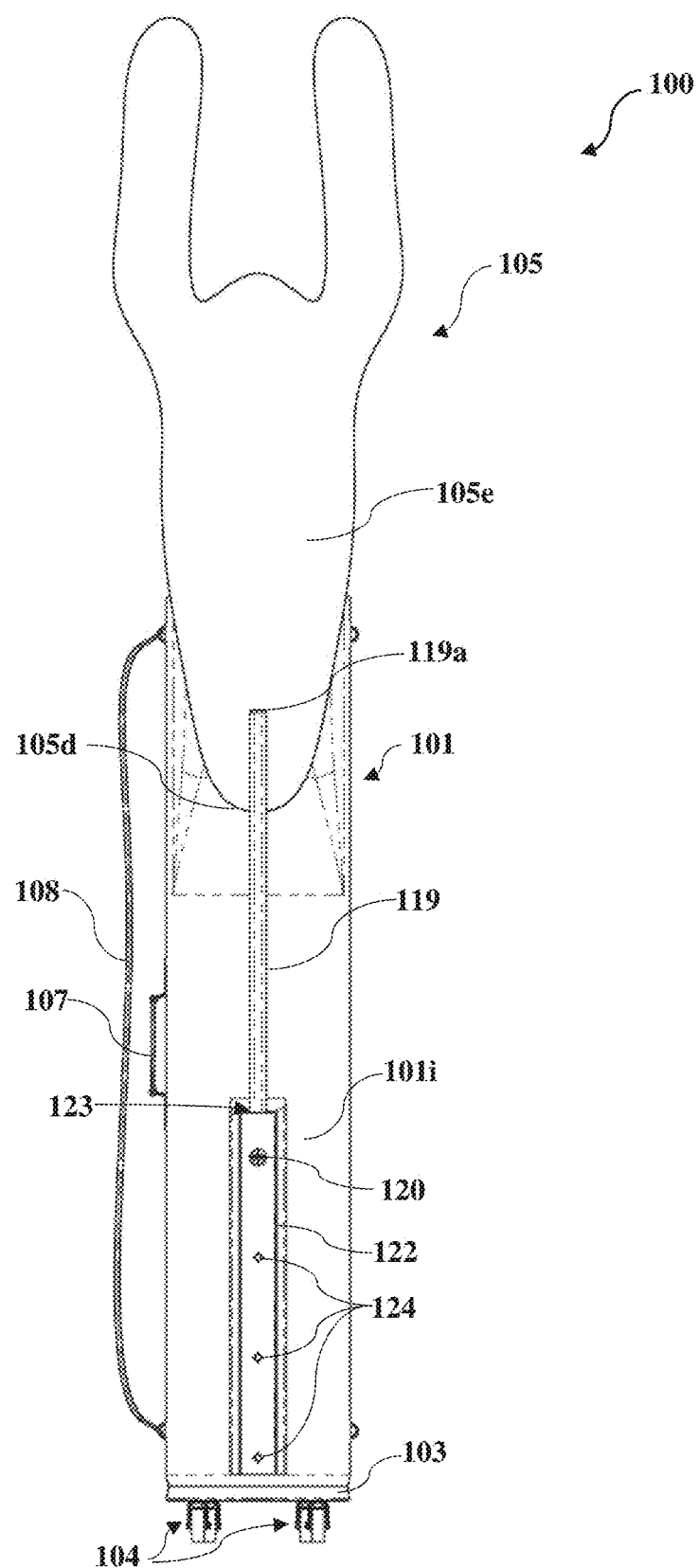
FIG. 6B exemplarily illustrates a rear elevation view of the portable sports rack and delivery system shown in FIG. 1.

FIGS. 6A-6B exemplarily illustrate a rear perspective view and a rear elevation view respectively, of the portable sports rack and delivery system 100 shown in FIG. 1. The rear views in FIGS. 6A-6B illustrate the attachment of the support member 119 extending from the training component 105 to the holder 122 attached to the rear section 101i of the elongate rack enclosure 101. The upper end 119a of the support member 119 is attached to the flat solid rear surface 105e of the support member 119, proximal to the lower end 105d of the training component 105. The distal lower end 119b of the support member 119 is inserted into the receptacle 123 of the holder 122 exemplarily illustrated in 2B and FIG. 7B, and secured to one of the openings 124 of the holder 122 using, for example, a lock pin 120.

FIG. 7A exemplarily illustrates a front elevation view of the portable sports rack and delivery system 100 shown in FIG. 1. The front elevation view in FIG. 7A illustrates the front section 101h of the elongate rack enclosure 101 with the delivery opening 102, the base member 103, the wheel assemblies, for example, the casters 104, the training component 105, the handle elements 107 and 108, and the pockets 110a, 110b, 110c, 110d, and 110e of the portable sports rack and delivery system 100. The front elevation view in 7A also illustrates the zippers 111a, 111b, 111c, 111d, and 111e configured to secure the pockets 110a, 110b, 110c, 110d, and 110e respectively. In an embodiment, the pockets 110a, 110b, 110c, 110d, and 110e are non-separating, closed-end pockets secured by the zippers 111a, 111b, 111c, 111d, and 111e respectively. The zippers 111a and 111b, in an open condition, create a partial flap in the pockets 110a and 110b respectively, for convenient insertion and retrieval of items and accessories of sports equipment. Each of the zippers 111c, 111d, and 111e, in an open condition, creates a small opening in each of the pockets 110c, 110d, and 110e respectively, for insertion and retrieval of items and accessories of sports equipment. In an embodiment, the portable sports rack and delivery system 100 further comprises foot members 121a and 121b configured to support the portable sports rack and delivery system 100 on a surface, for example, a ground surface, when the portable sports rack and delivery system 100 is oriented in a substantially horizontal position. In an embodiment as exemplarily illustrated in FIG. 7A, the foot members 121a and 121b are positioned on the left side 101e of the elongate rack enclosure 101. A user, for example, a sportsperson, may lift and carry the horizontally oriented portable sports rack and delivery system 100 using the bag handle 107.

FIG. 7B exemplarily illustrates a cross-sectional view of the portable sports rack and delivery system 100 taken along a section A-A shown in FIG. 7A. The cross-sectional view in FIG. 7B exemplarily illustrates the storage space 101g of the elongate rack enclosure 101, ball-shaped sports equipment, for example, the basketballs 112a, 112b, 112c, 112d, and 112e accommodated therewithin, the training component 105, and two of the wheel assemblies, for example, the casters 104, extending from the bottom surface 103a of the base member 103. In an example, the thickness of the walls 101j and 101k of the elongate rack enclosure 101 exemplarily illustrated in FIG. 7B is about 1.5 inches. The cross-sectional view in FIG. 7B also exemplarily illustrates the release component 115 comprising the spring base 114 loaded with the compression spring 113. The release component 115 is disposed and accommodated in the storage space 101g of the elongate rack enclosure 101 at the lower end 101b of the elongate rack enclosure 101. The compression spring 113 is, for example, an open-coil helical spring. The compression spring 113 comprises a first end 113a and a second end 113b. The first end 113a of the compression spring 113 is operably coupled to the base member 103. The second end 113b of the compression spring 113 is operably coupled to the spring base 114. As exemplarily illustrated in FIG. 7B, a predetermined number of balls, for example, five basketballs 112a, 112b, 112c, 112d, and 112e, are stored in a substantially vertical orientation within the storage space 101g of the elongate rack enclosure 101. The uppermost basketball 112a extends outwardly from the delivery opening 102 at the upper end 101a of the elongate rack enclosure 101. The lowermost basketball 112e is positioned and accommodated on the curved upper surface 114a of the spring base 114. The spring base 114, in operable communication with the compression spring 113, is configured to elevate the stacked basketballs 112b, 112c, 112d, and 112e remaining in the storage space 101g of the elongate rack enclosure 101 towards the delivery opening 102 when the uppermost basketball 112a is removed from the storage space 101g through the delivery opening 102 by a sportsperson, for example, a basketball player, a coach, a trainer, etc.

The compression spring 113 of the release component 115 is configured to resist compressive threes applied to the compression spring 113 by the load of the basketballs 112a, 112b, 112c, 112d, and 112e. When the uppermost basketball 112a is removed from the storage space 101g through the delivery opening 102 and a force is applied to the compression spring 113, the compression spring 113 condenses or compresses, storing the force until the force is released to elevate the remaining basketballs 112b, 112c, 112d, and 112d such that the next uppermost basketball 112b is released from the storage space 101g of the elongate rack enclosure 101 for delivery through the delivery opening 102. When compressed in one direction, the compression spring 113 exerts force in the opposite direction as the compression spring 113 attempts to return to its resting length. The spring base 114 loaded with the compression spring 113 keeps the uppermost basketball, for example, 112a, at the upper end 101a of the elongate rack enclosure 101, so that when the uppermost basketball 112a is unloaded or removed from the storage space 101g through the delivery opening 102, the spring base 114, in operable communication with the compression spring 113, elevates the remaining basketballs 112b, 112c, 112d, and 112e to save the user, for example, a sportsperson, from bending down into the storage space 101g of the elongate rack enclosure 101 to retrieve the next uppermost basketball 112b. The compression spring 113 takes the strain out of loading and/or unloading basketballs 112a, 112b, 112c, 112d, and 112e or other sports equipment by lowering the load as sports equipment are added to the storage space 101g of the elongate rack enclosure 101, and elevates the sports equipment as each item or piece of sports equipment is removed from the delivery opening 102. When the user takes the uppermost basketball 112a out of the storage space 101g of the elongate rack enclosure 101, the release component 115 elevates the next uppermost basketball 112b for ready retrieval.

Figure 7C:
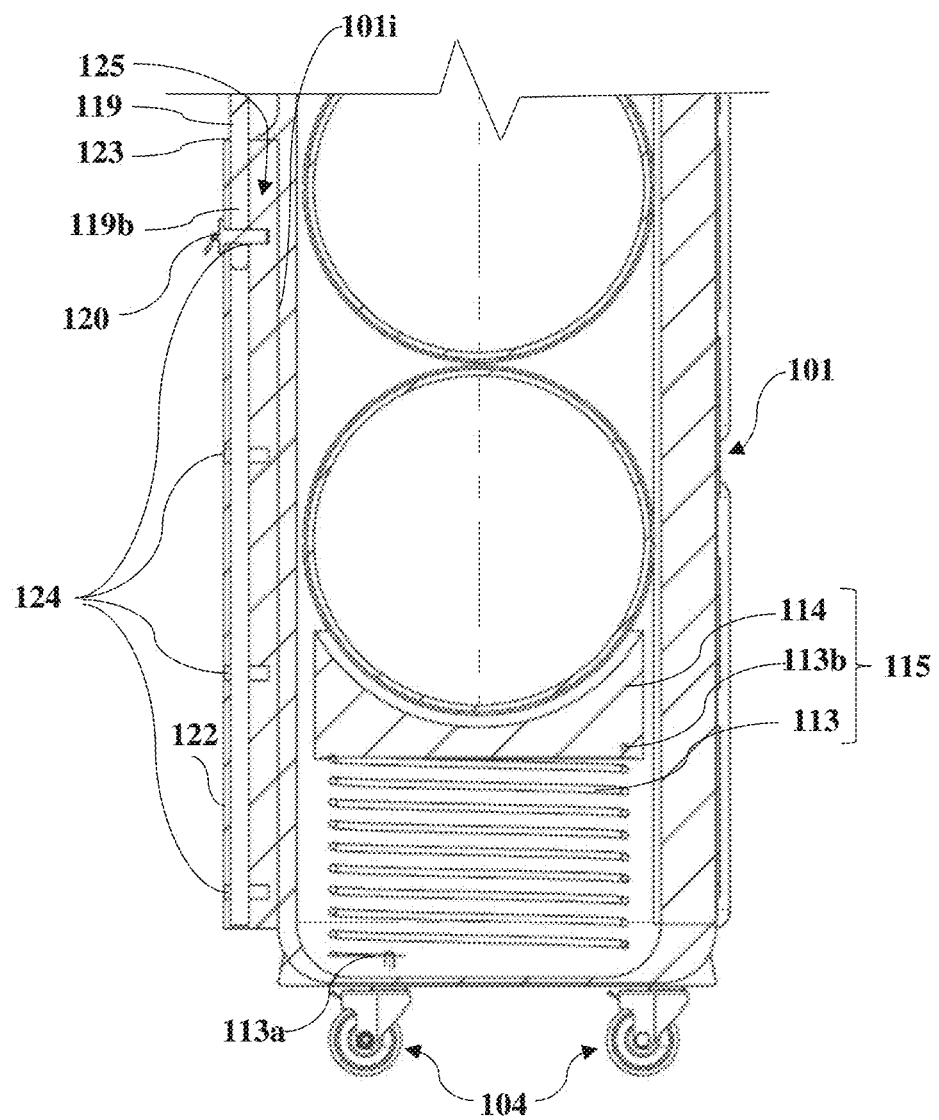
FIG. 7C exemplarily illustrates an enlarged view of a bottom half of the portable sports rack and delivery system shown in FIG. 7B, showing a holder configured to accommodate and secure a support member of the training component.

FIG. 7C exemplarily illustrates an enlarged view of a bottom half of the portable sports rack and delivery system 100 shown in FIG. 7B, showing the holder 122 configured to accommodate and secure the support member 119 of the training component 105. In an embodiment, the holder 122 comprises a holding space 125 and openings 124 spaced at predetermined intervals along the length of the holder 122. The holder 122 is configured to accommodate and secure the support member 119 of the training component 105 in the holding space 125 at a required height by inserting a fastener, for example, a lock pin 120, through the opening 119c of the support member 119 exemplarily illustrated in FIGS. 2A-3, and through one of the openings 124 of the holder 122. The height of the training component 105 is adjusted by sliding the support member 119 in the holding space 125 of the holder 122 in an upward position or a downward position and securing the support member 119 to one of the openings 124 of the holder 122 at the required height using the lock pin 120. In an example, the height to which the training component 105 is adjustable ranges, for example, from about 6 feet or 72 inches to about 8 feet or 96 inches. When not in use, the lock pin 120 is removed from one of the openings 124 of the holder 122, and the support member 119, extending from the training component 105, is removed from the holder 122 and stored external to the portable sports rack and delivery system 100.

Figure 8:
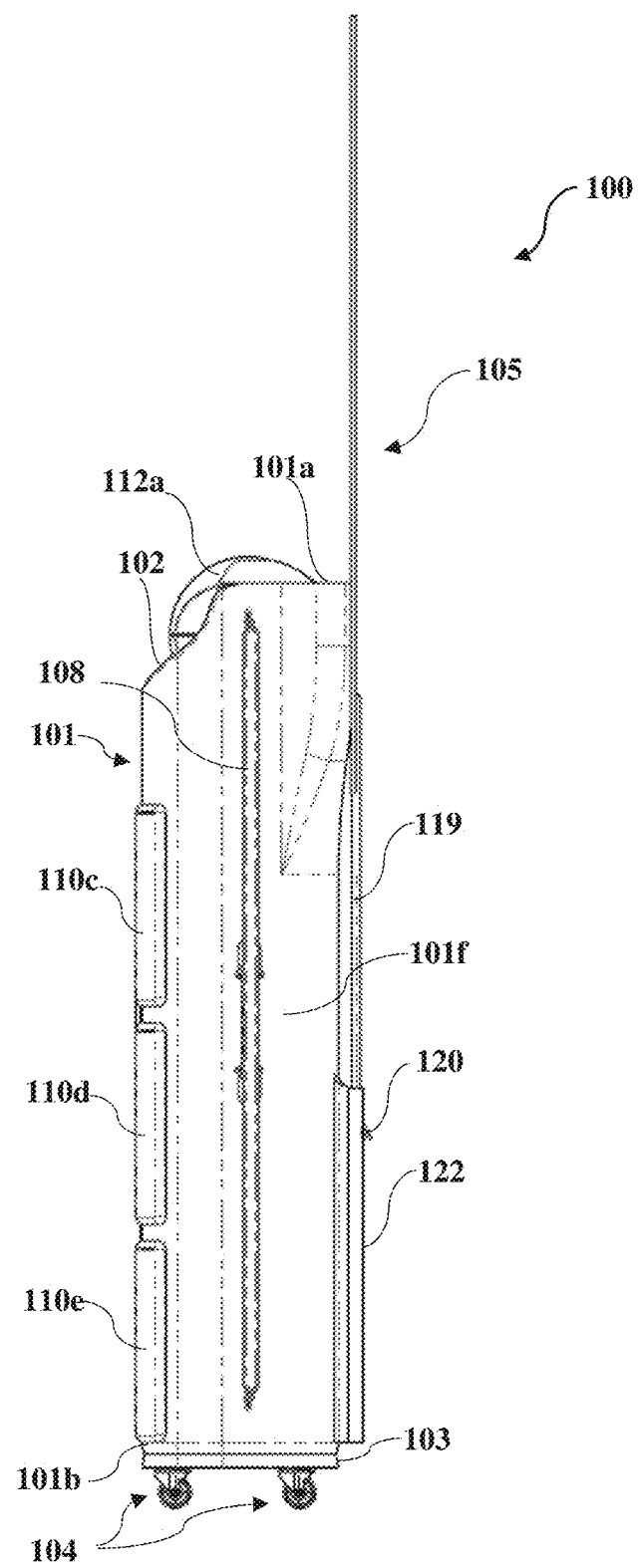
FIG. 8 exemplarily illustrates a right-side elevation view of the portable sports rack and delivery system shown in FIG. 1.

FIG. 8 exemplarily illustrates a right-side elevation view of the portable sports rack and delivery system 100 shown in FIG. 1. The right-side elevation view in FIG. 8 exemplarily illustrates the elongate rack enclosure 101; the uppermost basketball 112a extending outwardly from the delivery opening 102 of the elongate rack enclosure 101; the elongate strap 108 positioned on the right side 101f of the elongate rack enclosure 101 for gripping and carrying the portable sports rack and delivery system 100; the training component 105 with its support member 119 slidably connected within its holder 122; the pockets 110c, 11.0d, and 110e configured to store items and accessories of sports equipment; and two of the wheel assemblies, for example, the casters 104, extending from the base member 103.

Figure 9:
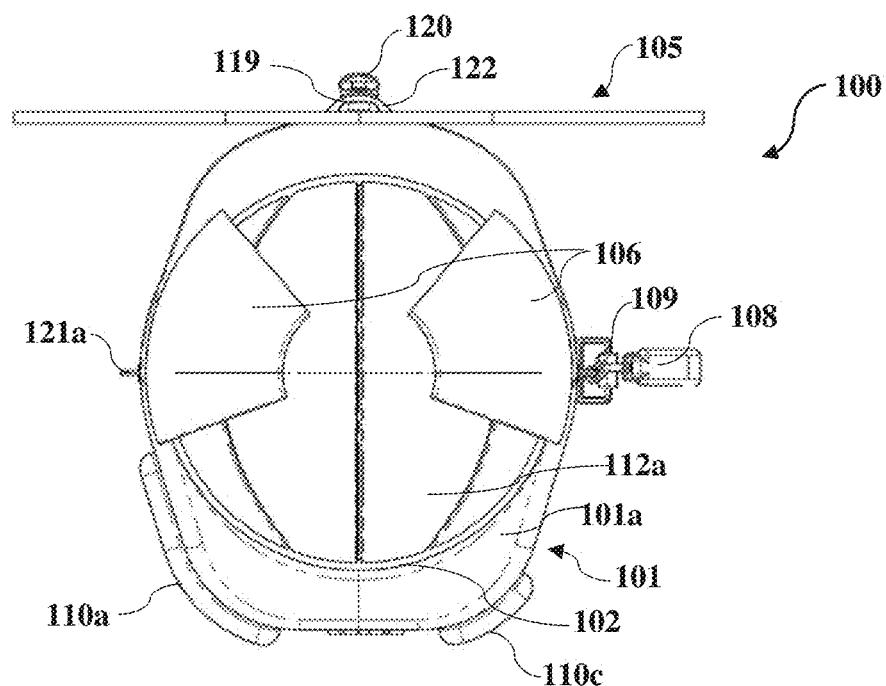
FIG. 9 exemplarily illustrates a top plan view of the portable sports rack and delivery system shown in FIG. 1.

FIG. 9 exemplarily illustrates a top plan view of the portable sports rack and delivery system 100 shown in FIG. 1. The top plan view in FIG. 9 exemplarily illustrates the delivery opening 102 at the upper end 101a of the elongate rack enclosure 101, the stopper elements 106 configured to secure and contain the uppermost basketball 112a extending outwardly from the delivery opening 102; the elongate strap 108 connected to the elongate rack enclosure 101 using the connector element 109 and configured for gripping and carrying the portable sports rack and delivery system 100; the training component 105 with its support member 119 slidably connected within its holder 122; the different-sized pockets 110a and 110c with different storage capacities to store items and accessories of sports equipment; and one of the foot members 121a configured to support the portable sports rack and delivery system 100 when oriented in a substantially horizontal position and placed on a surface. As exemplarily illustrated in FIG. 9, the stopper elements 106 partially cover the delivery opening 102.

Figure 10:
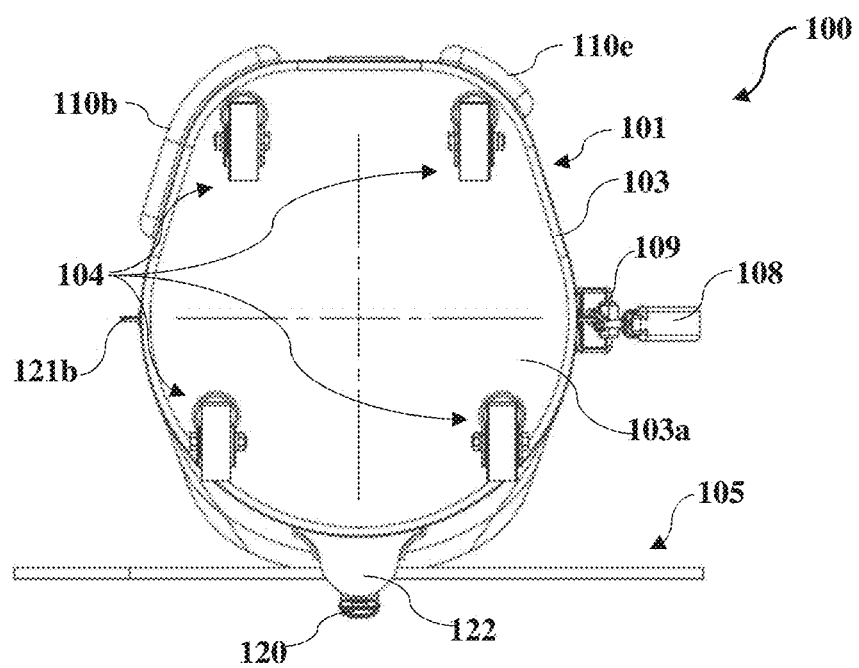
FIG. 10 exemplarily illustrates a bottom elevation view of the portable sports rack and delivery system shown in FIG. 1.

FIG. 10 exemplarily illustrates a bottom elevation view of the portable sports rack and delivery system 100 shown in FIG. 1. The bottom elevation view in FIG. 10 exemplarily illustrates the bottom surface 103a of the base member 103, the wheel assemblies, for example, the casters 104, operably coupled to the bottom surface 103a of the base member 103; the elongate strap 108 connected to the elongate rack enclosure 101 using the connector element 109 and configured for gripping and carrying the portable sports rack and delivery system 100; the training component 105 and its holder 122; the different-sized pockets 110b and 110e with different storage capacities to store items and accessories of sports equipment; and one of the foot members 121b configured to support the portable sports rack and delivery system 100 when oriented in a substantially horizontal position and placed on a surface.

Figure 11A:
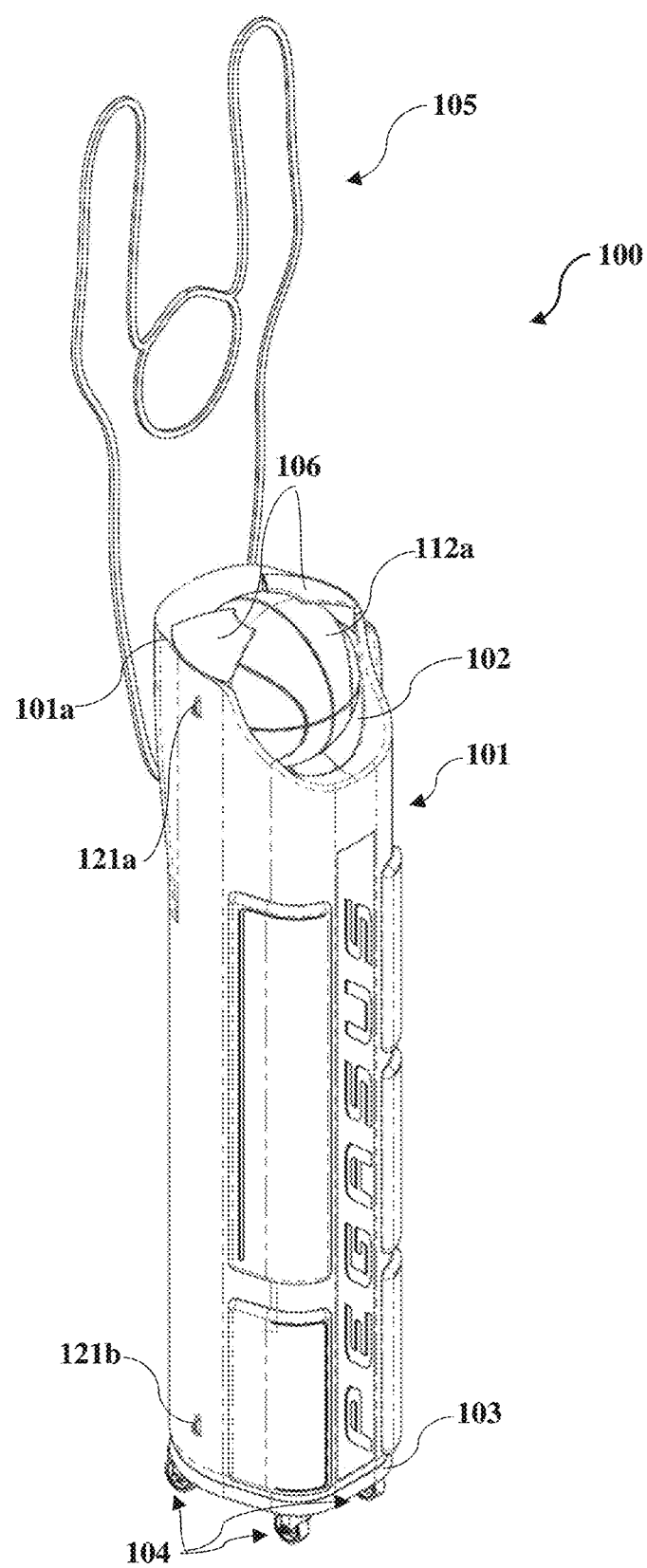
FIG. 11A exemplarily illustrates a left-side, perspective view of an embodiment of the portable sports rack and delivery system, showing an uppermost ball partially covered and contained by stopper elements.

FIG. 11A exemplarily illustrates a left-side, perspective view of an embodiment of the portable sports rack and delivery system 100, showing an uppermost ball, for example, an uppermost basketball 112a, partially covered and contained by the stopper elements 106. Prior to use and operation of the portable sports rack and delivery system 100, ball-shaped equipment, for example, basketballs 112a, 112b, 112c, 112d, and 112e, are stacked substantially vertically, one above the other, and stored in the storage space 101g of the elongate rack enclosure 101 as exemplarily illustrated in FIG. 7B. The stopper elements 106 attached to the upper end 101a of the elongate rack enclosure 101, for example, by a snap-fit connection, secure and contain the uppermost basketball 112a extending outwardly from the delivery opening 102 of the elongate rack enclosure 101 as exemplarily illustrated in FIG. 11A. The stopper elements 106 preclude the uppermost basketball 112a from rolling out of the storage space 101g of the elongate rack enclosure 101.

Figure 11B:
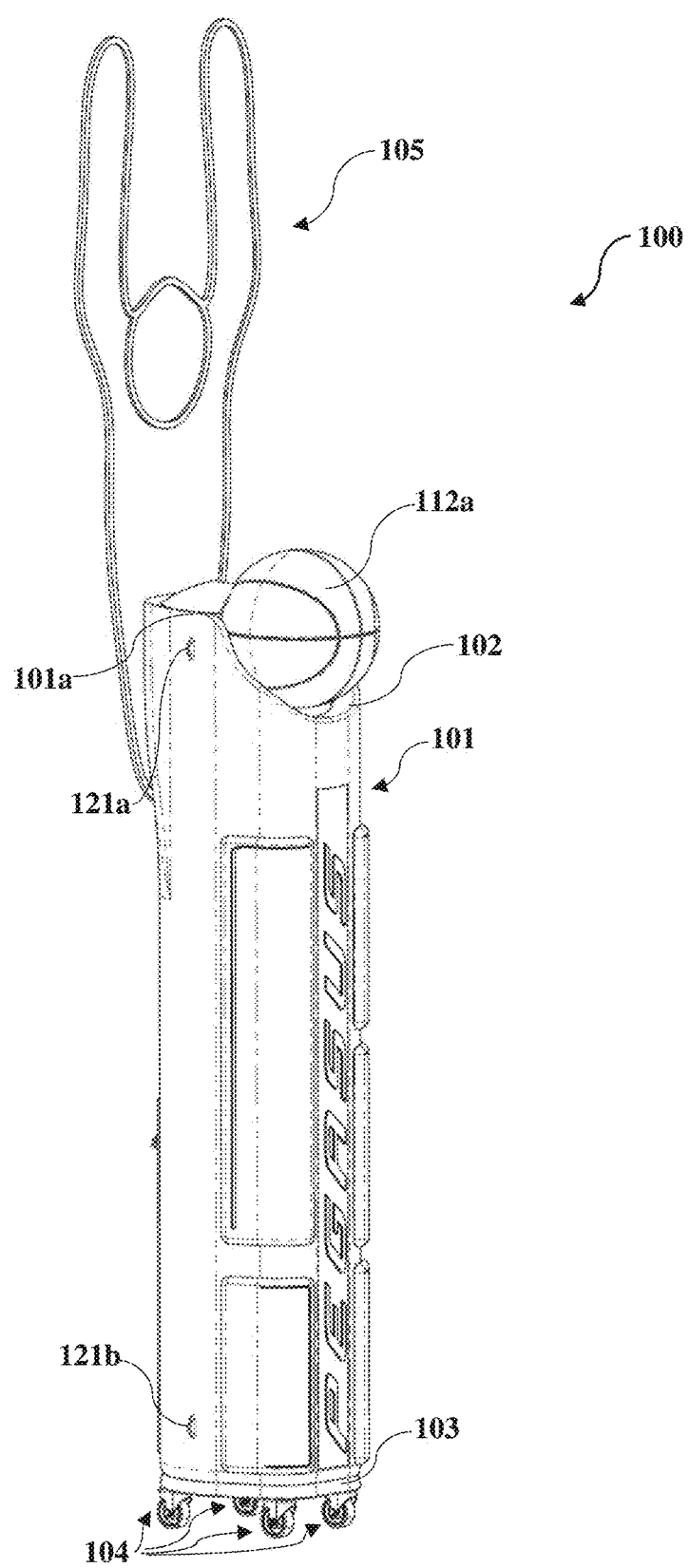
FIG. 11B exemplarily illustrates a left-side, perspective view of an embodiment of the portable sports rack and delivery system, showing an uppermost ball released from a storage space of an elongate rack enclosure for delivery through a delivery opening of the portable sports rack and delivery system.

FIG. 11B exemplarily illustrates a left-side, perspective view of an embodiment of the portable sports rack and delivery system 100, showing an uppermost ball, for example, an uppermost basketball 112a, released from the storage space 101g of the elongate rack enclosure 101 exemplarily illustrated in FIG. 7B, for delivery through the delivery opening 102 of the portable sports rack and delivery system 100. During operation of the portable sports rack and delivery system 100, the stopper elements 106 exemplarily illustrated in FIG. 11A, are removed from their attachment, for example, snap-fit connection, at the upper end 101a of the elongate rack enclosure 101, thereby allowing the uppermost basketball 112a to be released through the delivery opening 102 of the elongate rack enclosure 101 as exemplarily illustrated in FIG. 11B. When the uppermost basketball 112a is released and delivered through the delivery opening 102 to a sportsperson, for example, a basketball player, the spring base 114, in operable communication with the compression spring 113 exemplarily illustrated in FIG. 7B, elevates the next uppermost basketball 112b towards the delivery opening 102 for subsequent release and delivery through the delivery opening 102. Similarly, all the remaining basketballs, for example, 112c, 112d, and 112e exemplarily illustrated in FIG. 7B, are elevated, released, and delivered through the delivery opening 102 from the storage space 101g of the elongate rack enclosure 101 of the portable sports rack and delivery system 100.

Figure 12A:
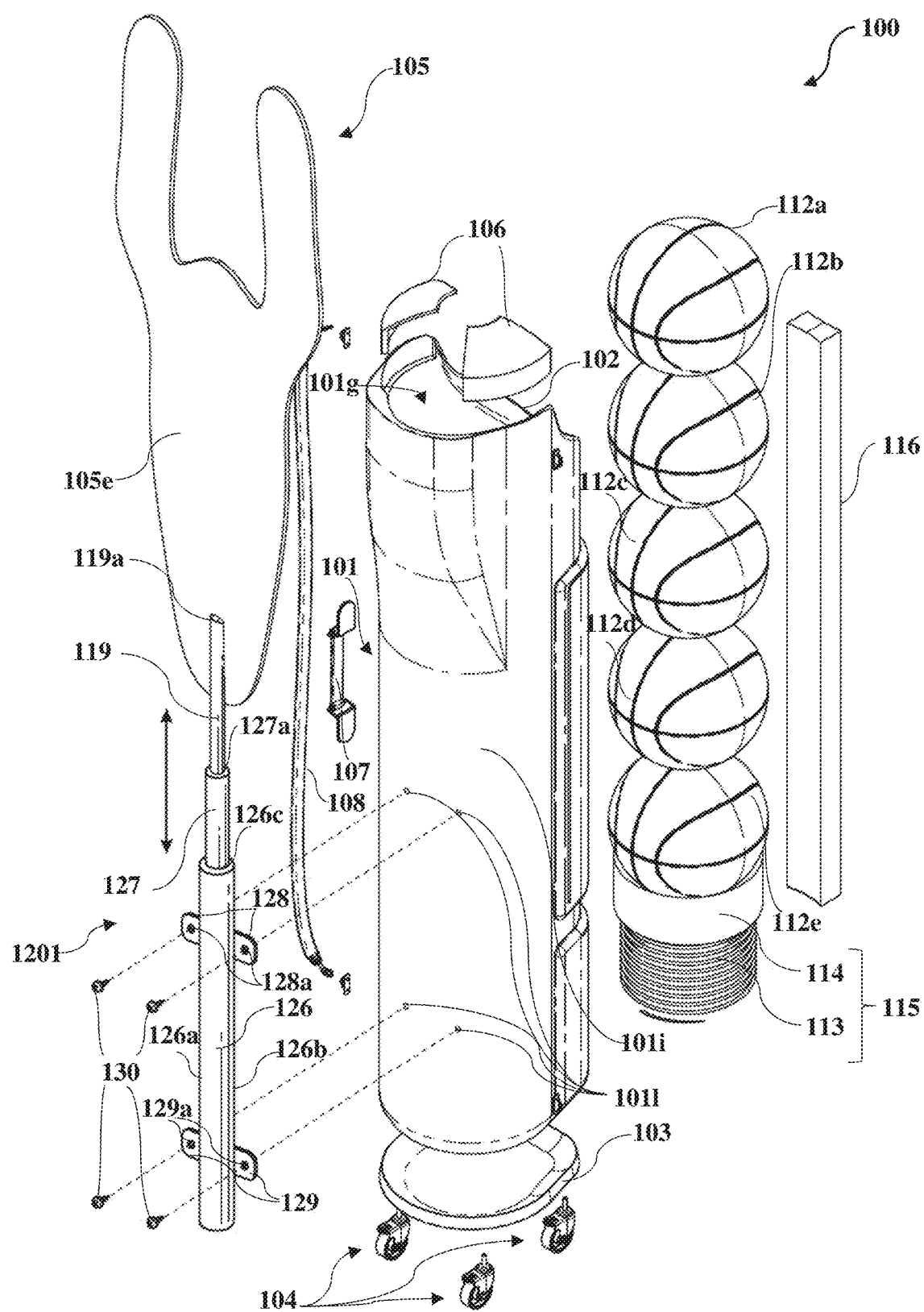
FIGS. 12A-12B exemplarily illustrate rear perspective, exploded views of an embodiment of the portable sports rack and delivery system, showing an adjustable coupling of the training component to a rear section of the elongate rack enclosure using a telescopic assembly.
Figure 12B:
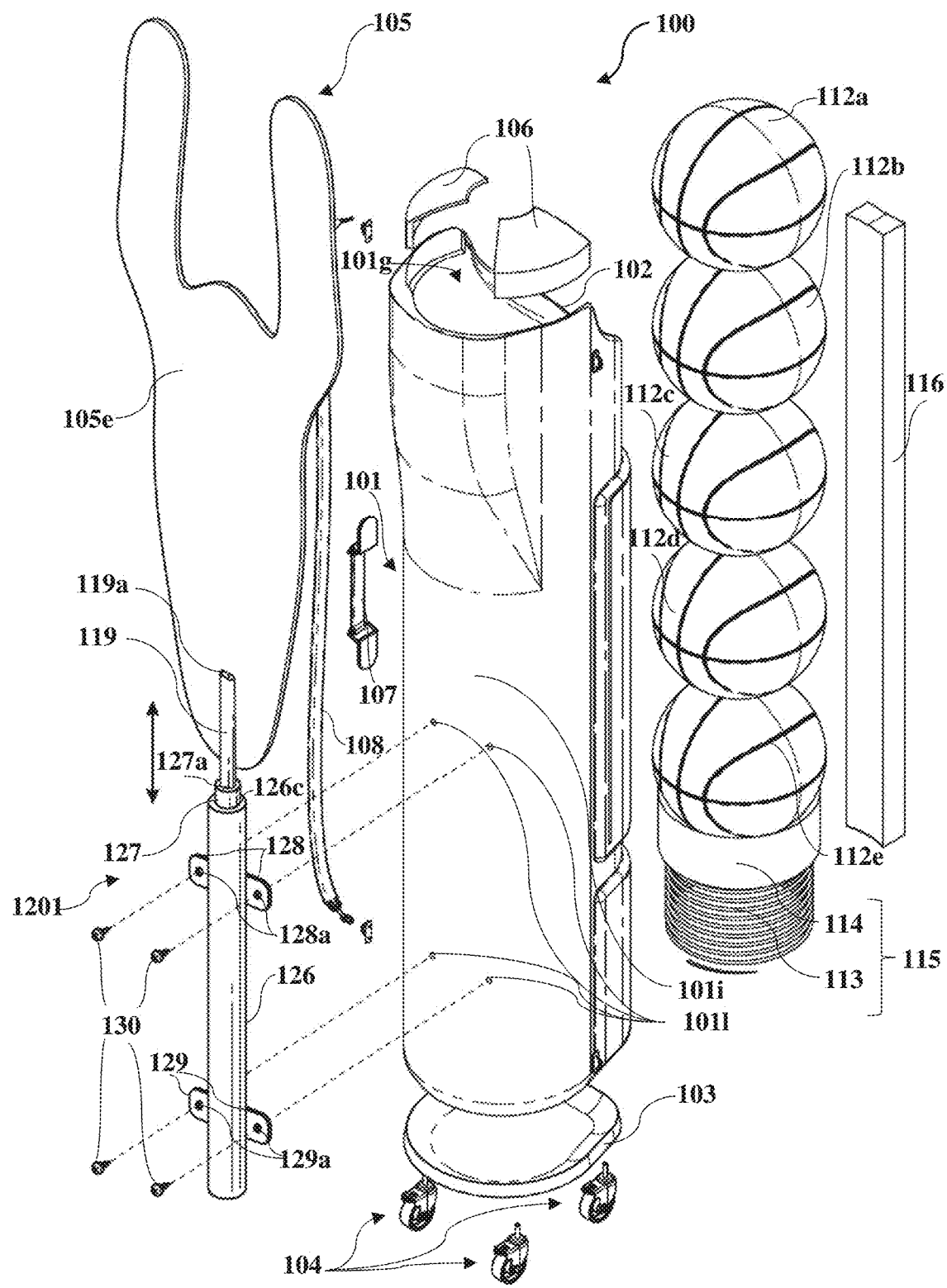

FIGS. 12A-12B exemplarily illustrate rear perspective, exploded views of an embodiment of the portable sports rack and delivery system 100, showing an adjustable coupling of the training component 105 to the rear section 101i of the elongate rack enclosure 101 using a telescopic assembly 1201. In this embodiment, the training component 105 is adjustably coupled to the rear section 101i of the elongate rack enclosure 101 using the telescopic assembly 1201. The telescopic assembly 1201 comprises an inner telescopic member 127 telescopically connected to an outer telescopic member 126 via an opening 126c in the outer telescopic member 126. In an embodiment, the inner telescopic member 127 and the outer telescopic member 126 of the telescopic assembly 1201 are, for example, hollow cylindrical structures. The inner telescopic member 127 is movable and slides within the outer telescopic member 126. The telescopic assembly 1201 is securely attached to the rear section 101i of the elongate rack enclosure 101 via flanges 128 and 129 of the outer telescopic member 126. The flanges 128 and 129 extend from opposing sides 126a and 126b of the outer telescopic member 126. The flanges 128 and 129 comprise openings 128a and 129a respectively, for inserting fasteners 130, for example, screws. The telescopic assembly 1201 is securely attached to the rear section 101i of the elongate rack enclosure 101 by inserting the fasteners 130 into the openings 128a and 129a of the flanges 128 and 129 of the outer telescopic member 126 and into the corresponding openings 101l configured on the rear section 101i of the elongate rack enclosure 101.

The support member 119 of the training component 105 is inserted into an opening 127a of the inner telescopic member 127 of the telescopic assembly 1201. The height of the training component 105 is increased by moving or extending the inner telescopic member 127 from within the outer telescopic member 126 in an upward direction as exemplarily illustrated in FIG. 12A. The height of the training component 105 is decreased by moving or retracting the inner telescopic member 127 into the outer telescopic member 126 in a downward direction as exemplarily illustrated in FIG. 12B. In an embodiment, the training component 105 is locked at a required height using a locking mechanism, for example, a push button locking system (not shown). The push button locking system comprises a push button (not shown) operably coupled on an outer surface of the inner telescopic member 127 and openings (not shown) configured at predetermined intervals in the outer telescopic member 126. The openings in the outer telescopic member 126 correspond to different heights at which the training component 105 can be secured. When an operator of the portable sports rack and delivery system 100, for example, a coach or a trainer, wishes to adjust the height of the training component 105, the operator extends the inner telescopic member 127 that holds the support member 119 of the training component 105 in an upward direction such that the push button, that is in a compressed condition, is released into one of the openings in the outer telescopic member 126 corresponding to the required height, thereby locking the training component 105 at the required height.

To readjust the height, the operator presses the push button from the opening in the outer telescopic member 126, which allows the inner telescopic member 127 to slide in an upward direction inside the outer telescopic member 126 with the push button in the compressed condition. The operator extends the inner telescopic member 127 to the next opening in the outer telescopic member 126 corresponding to the required height. On reaching the opening at the required height, the push button is released into the opening in the outer telescopic member 126, thereby locking the training component 105 at the required height. Similarly, the operator readjusts the height of the training component 105 by pressing the push button from the opening in the outer telescopic member 126, which allows the inner telescopic member 127 to slide in a downward direction inside the outer telescopic member 126 with the push button in the compressed condition. The operator lowers the inner telescopic member 127 to the next opening in the outer telescopic member 126 corresponding to the required height. On reaching the opening at the required height, the push button is released into the opening in the outer telescopic member 126, thereby locking the training component 105 at the required height. In other embodiments, other functionally equivalent methods and mechanisms for locking the training component 105 at a required height are used.

FIGS. 13A-13D exemplarily illustrate front perspective views of an embodiment of the portable sports rack and delivery system 100, showing an implementation of a delivery system 1301 operably coupled to the release component 115 for delivering an uppermost ball, for example, an uppermost basketball 112a, from the storage space 101g of the elongate rack enclosure 101 to the delivery opening 102. In an embodiment, the delivery system 1301 comprises a guide element 131 and a lever 133. The guide element 131 extends along a length of the elongate rack enclosure 101. The guide element 131 defines a channel 132 extending therewithin along the length of the elongate rack enclosure 101. The channel 132 extends between an upper end 131a and a lower end 131b of the guide element 131. The lever 133 comprises a first end (not shown) and a second end 133a. The first end of the lever 133 is connected to the release component 115. For example, the first end of the lever 133 is connected to an opening 135 configured on the spring base 114 of the release component 115 as exemplarily illustrated in FIGS. 13A-13B. The second end 133a of the lever 133 extends outwardly from the channel 132 of the guide element 131. In an embodiment, a knob 134 of, for example, a spherical shape, configured as a handle, is attached to the second end 133a of the lever 133 as exemplarily illustrated in FIGS. 13A-13D, for allowing manual operation of the lever 133.

The lever 133 is configured to traverse the channel 132 of the guide element 131 vertically and move the release component 115 in an upward direction from the lower end 101b of the elongate rack enclosure 101 towards the delivery opening 102 at the upper end 101a of the elongate rack enclosure 101 for delivering the uppermost basketball 112a from the storage space 101g of the elongate rack enclosure 101. As exemplarily illustrated in FIGS. 13A-13B, the basketballs 112a, 112b, 112c, 112d, and 112e are stacked substantially vertically, one above the other on the spring base 114. When the uppermost basketball 112a is removed from the storage space 101g through the delivery opening 102, an operator of the portable sports rack and delivery system 100 grips the lever 133 via the knob 134 and moves the lever 133 in an upward direction along the channel 132 of the guide element 131 to elevate the stacked basketballs 112b, 112c, 112d, and 112e remaining in the storage space 101g of the elongate rack enclosure 101 towards the delivery opening 102. Similarly, when the remaining basketballs, for example, 112b, 112c, 112d, are removed from the storage space 101g through the delivery opening 102, in order to access the last basketball 112e positioned on the spring base 114, the operator grips the lever 133 via the knob 134 and moves the lever 133 in an upward direction along the channel 132 of the guide element 131 to elevate the last basketball 112e remaining in the storage space 101g of the elongate rack enclosure 101 towards the delivery opening 102 as exemplarily illustrated in FIG. 13B.

Figure 13A:
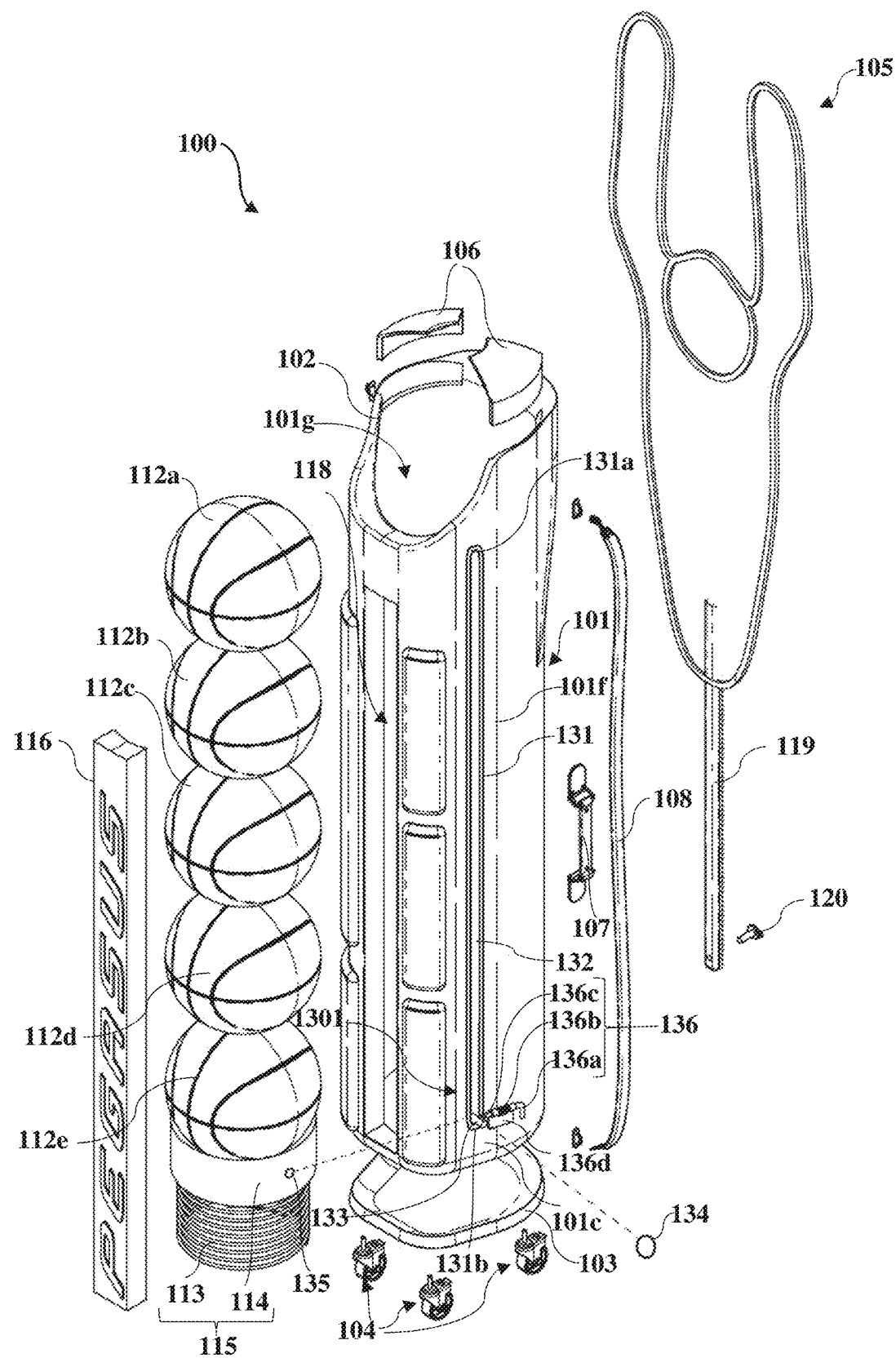
FIGS. 13A-13D exemplarily illustrate front perspective views of an embodiment of the portable sports rack and delivery system, showing an implementation of a delivery system operably coupled to a release component for delivering an uppermost ball from the storage space of the elongate rack enclosure to the delivery opening.
Figure 13B:
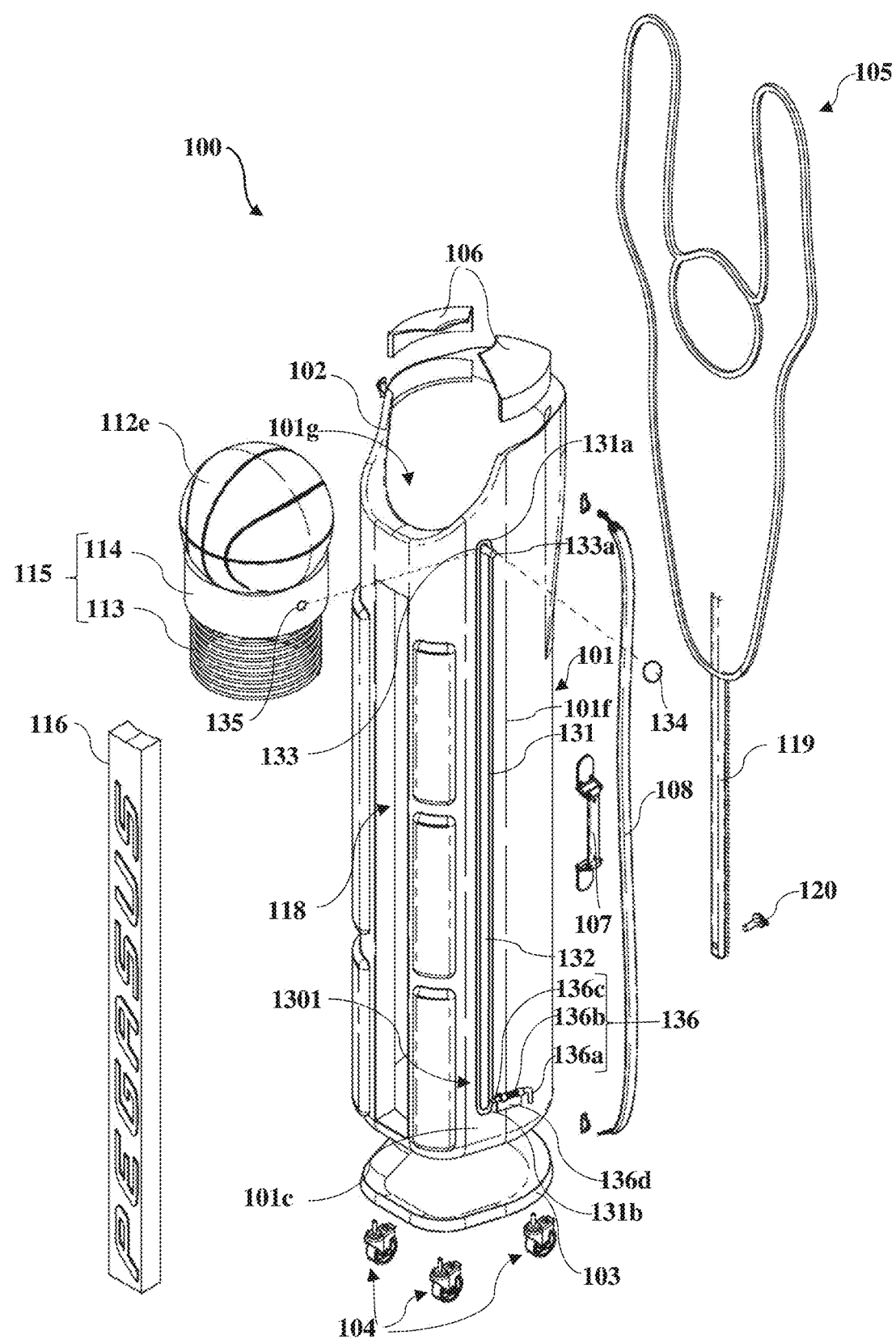
Figure 13C:
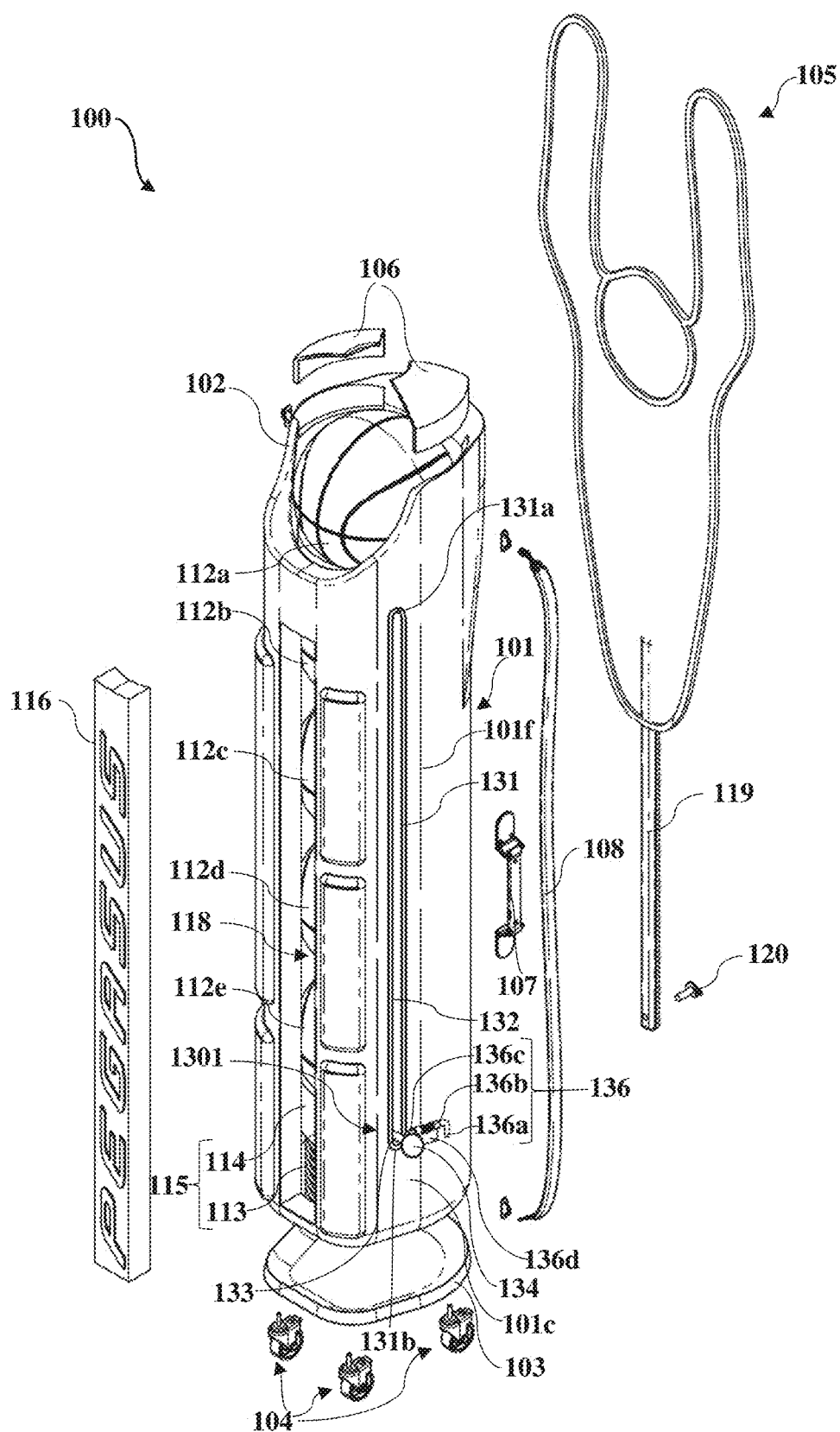
Figure 13D:
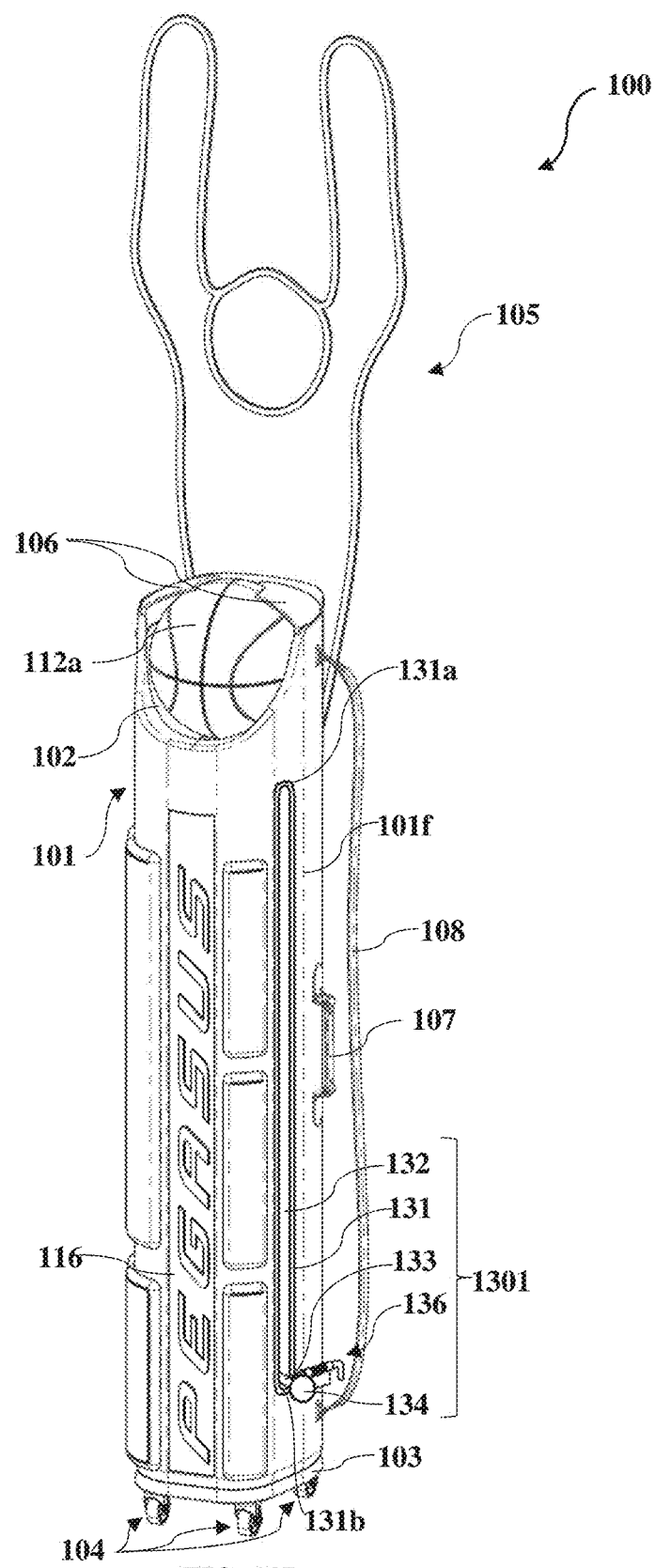

In an embodiment, the portable sports rack and delivery system 100 further comprises a locking member 136 attached to the lower end 131b of the guide element 131 proximal to the lower end 101b of the elongate rack enclosure 101. The locking member 136 is configured to lock the lever 133, and in turn, the compressed spring 113 of the release component 115, in position at the lower end 131b of the guide element 131 as exemplarily illustrated in FIGS. 13C-13D. In an embodiment, the locking member 136 is a spring-loaded latch comprising a plate 136d and a spring-loaded plunger 136b with a pin 136a at one end and a nose 136c at the other end. The plate 136d of the locking member 136 is attached proximal to the lower end 131b of the guide element 131 on the outer surface 101, of the elongate rack enclosure 101 as exemplarily illustrated in FIGS. 13A-13C, using fasteners, for example, screws, bolts, etc. When the basketballs 112a, 112b, 112c, 112d, and 112e are being loaded into the storage space 101g of the elongate rack enclosure 101, the release component 115 is locked at the lower end 101b of the elongate rack enclosure 101 using the locking member 136. In the locked position, the nose 136c of the spring-loaded plunger 136b is positioned over the second end 133a of the lever 133 as exemplarily illustrated in FIG. 13A and FIGS. 13C-13D. To operate the lever 133 and elevate the basketballs 112b, 112c, 112d, and 112e towards the delivery opening 102, the operator pulls the pin 136a of the spring-loaded plunger 136b, thereby releasing the lever 133 and allowing the lever 133 to vertically traverse the channel 132 of the guide element 131 in an upward direction and elevate the basketballs 112b, 112c, 112d, and 112e remaining in the storage space 101g of the elongate rack enclosure 101 towards the delivery opening 102. FIG. 13B exemplarily illustrates the last basketball 112e being elevated towards the delivery opening 102 using the lever 133. To elevate the last basketball 112e from the storage space 101g of the elongate rack enclosure 101 towards the delivery opening 102, the lever 133 is manually operated to vertically traverse the channel 132 of the guide element 131 in an upward direction till the lever 133 reaches the upper end 131a of the guide element 131 as exemplarily illustrated in FIG. 13B. The release component 115 is moved down towards the lower end 131b of the guide element 131 by pushing the lever 133 in a downward direction. On reaching the lower end 131b of the guide element 131, the locking member 136 locks the release component 115 at the lower end 101b of the elongate rack enclosure 101.

Figure 14A:
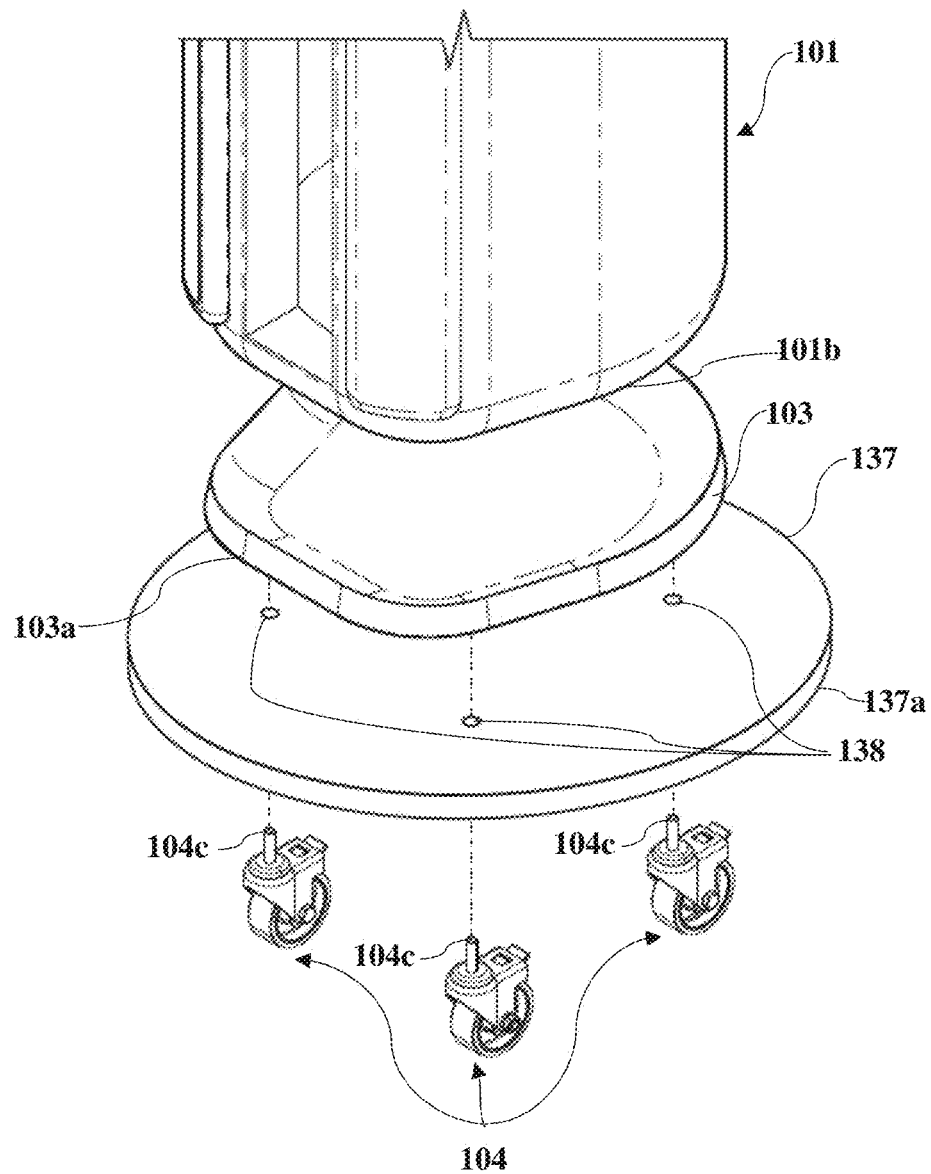
FIGS. 14A-14B exemplarily illustrate a partial perspective view of the elongate rack enclosure of an embodiment of the portable sports rack and delivery system, showing a plate member configured to preclude the elongate rack enclosure from tipping when the elongate rack enclosure is in a substantially vertical position.
Figure 14B:
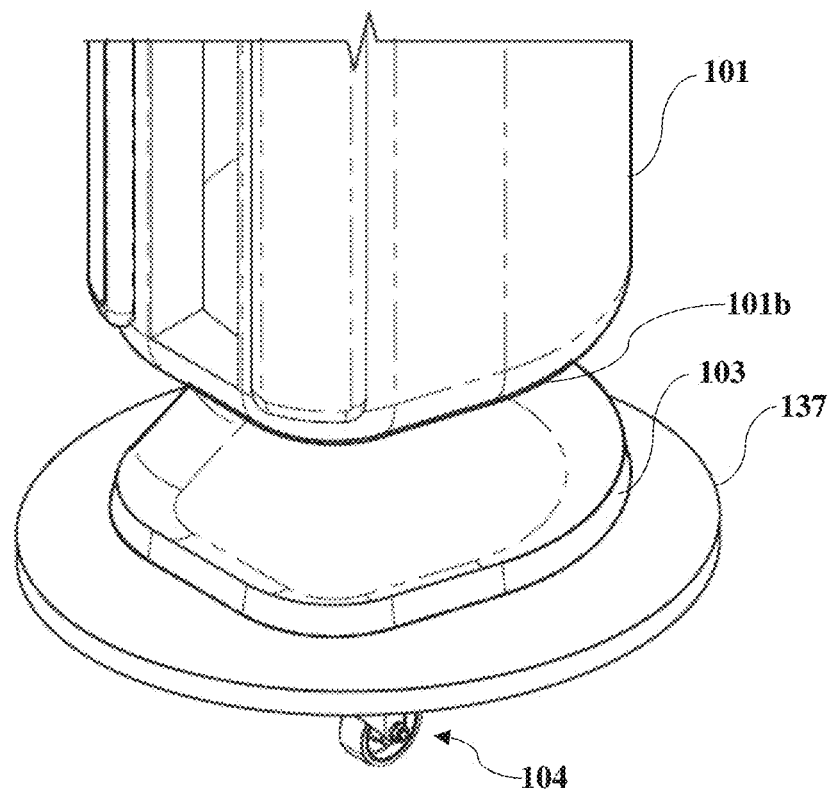

FIGS. 14A-14B exemplarily illustrate a partial perspective view of the elongate rack enclosure 101 of an embodiment of the portable sports rack and delivery system 100, showing a plate member 137 configured to preclude the elongate rack enclosure 101 from tipping when the elongate rack enclosure 101 is in a substantially vertical, upright position. In this embodiment, the plate member 137 is, for example, a circular plate, attached to the bottom surface 103a of the base member 103. In an embodiment as exemplarily illustrated in FIG. 14A, the plate member 137 comprises openings 138 through which the stems 104c of the wheel assemblies, for example, the casters 104, are inserted. In this embodiment, the casters 104 are positioned below a lower surface 137a of the plate member 137. The stems 104c of the casters 104 are then inserted into the openings 138 of the plate member 137 for attachment to the bottom surface 103a of the base member 103 of the portable sports rack and delivery system 100 as exemplarily illustrated in FIG. 14B.

The base member 103 is attached to the lower end 101b of the elongate rack enclosure 101. The plate member 137 is configured to stabilize the elongate rack enclosure 101 and preclude the elongate rack enclosure 101 from tipping when the elongate rack enclosure 101 is in a substantially vertical, upright position. In an embodiment, the plate member 137 is configured to touch a ground surface or have a minimum clearance from the ground surface.

Figure 15A:
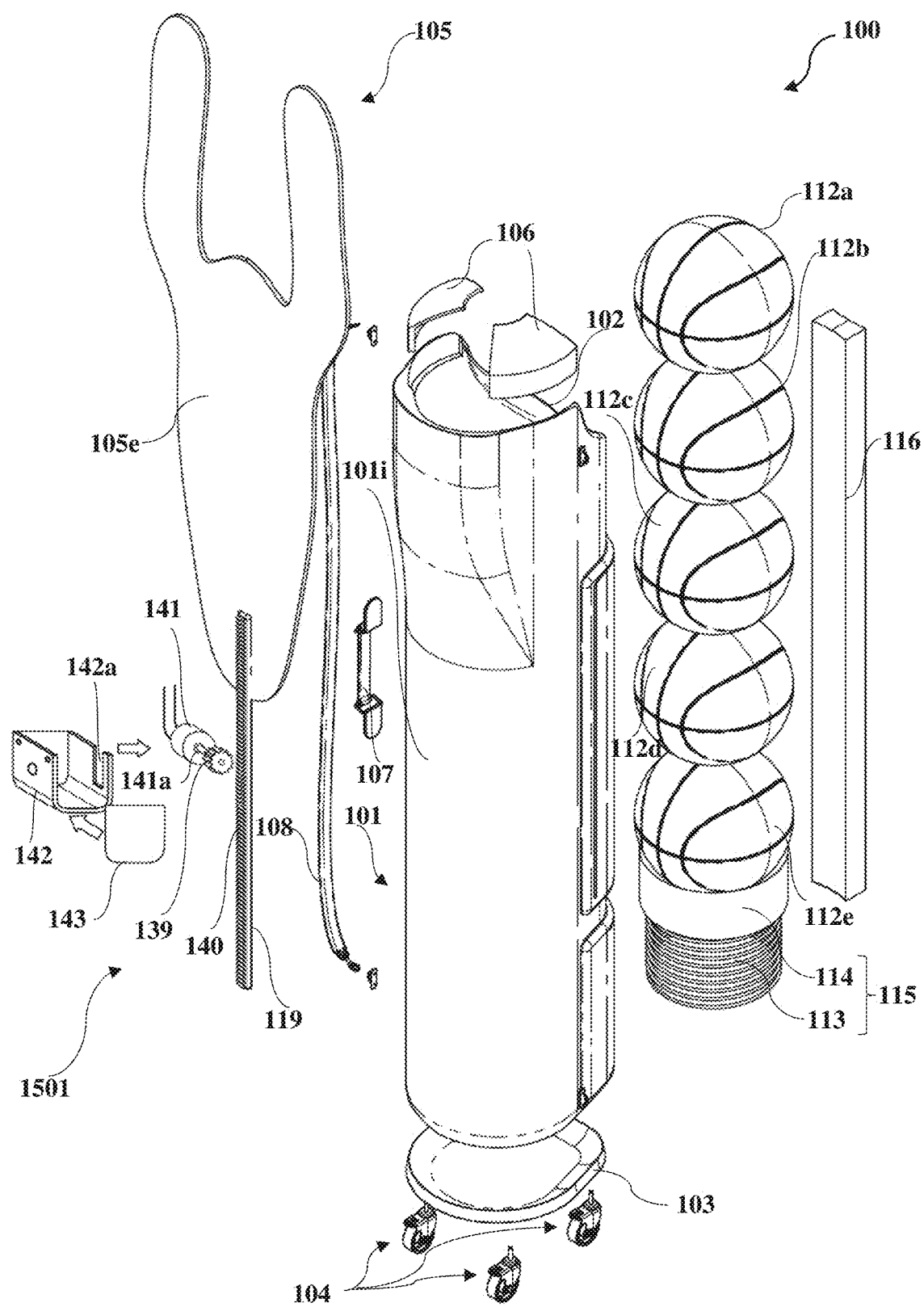
FIGS. 15A-15C exemplarily illustrate rear perspective, exploded views of an embodiment of the portable sports rack and delivery system, showing a gear system operably coupled to the training component for moving the training component in an upward direction and a downward direction.
Figure 15B:
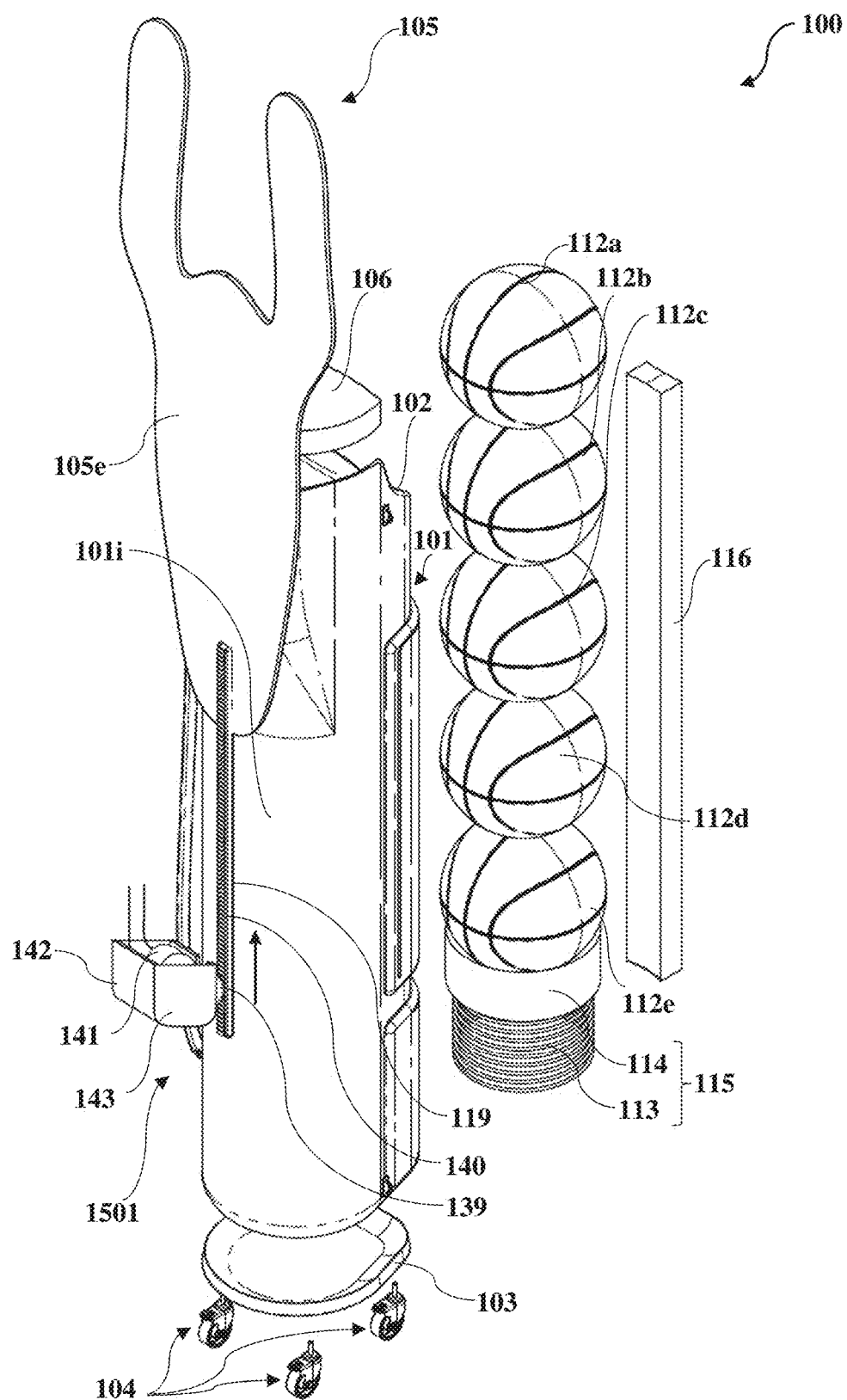
Figure 15C:
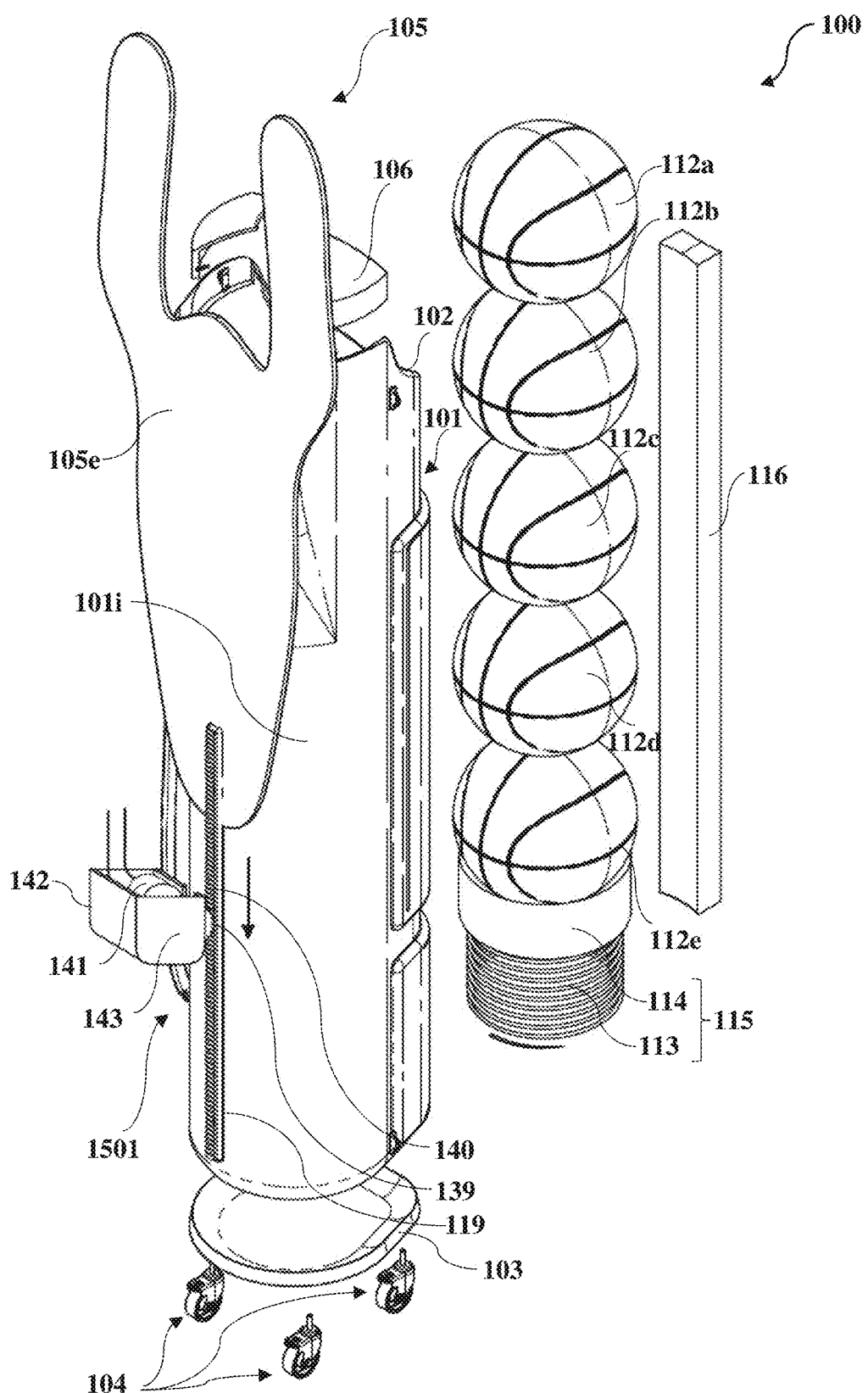

FIGS. 15A-15C exemplarily illustrate rear perspective, exploded views of an embodiment of the portable sports rack and delivery system 100, showing a gear system 1501 operably coupled to the training component 105 for moving the training component 105 in an upward direction and a downward direction. In this embodiment, the gear system 1501 is operably coupled to and in engageable communication with the support member 119 of the training component 105 at the rear section 101i of the elongate rack enclosure 101. In an embodiment, the gear system 1501 is a rack and pinion system where a linear gear or a rack 140 is configured on the support member 119 of the training component 105 and a circular gear or a pinion 139 is positioned in a training control unit 142. The pinion 139 is operably coupled to a motor 141, for example, an electric motor, accommodated in the training control unit 142. The pinion 139 extends from a shaft 141a of the motor 141 as exemplarily illustrated in FIG. 15A. The training control unit 142 is configured as a box comprising a cover 143 for securely housing the motor 141 with the pinion 139 therewithin. The training control unit 142 comprises a notch 142a through which the pinion 139 is exposed for engageably communicating with the rack 140 on the support member 119 of the training component 105. The training control unit 142 is attached to the rear section 101i of the elongate rack enclosure 101 using fasteners, such that the pinion 139 extending outwardly from the notch 142a of the training control unit 142 engages with teeth of the rack 140 on the support member 119 of the training component 105.

The gear system 1501, when activated, is configured to move the training component 105 in an upward direction and a downward direction to provide an obstruction to a trajectory of one of the basketballs 112a, 112b, 112c, 112d, and 112e thrown by a sportsperson, for example, a basketball player, to assist in training the sportsperson. When the motor 141 is powered on, for example, by a control button (not shown), the motor 141 rotates the pinion 139 via the shaft 141a, which engages the teeth of the rack 140 to move the rack 140 and in turn, the support member 119 of the training component 105, in an upward direction as exemplarily illustrated in FIG. 15B, and in a downward direction as exemplarily illustrated in FIG. 15C, to assist in training the sportsperson by simulating an obstruction to a trajectory of one of the basketballs 112a, 112b, 112c, 112d, and 112e thrown by the sportsperson. When the motor 141 is powered on, the rotational motion of the pinion 139 converts into linear motion of the rack 140, thereby moving the support member 119 of the training component 105 in an upward direction and a downward direction.

Figure 16A:
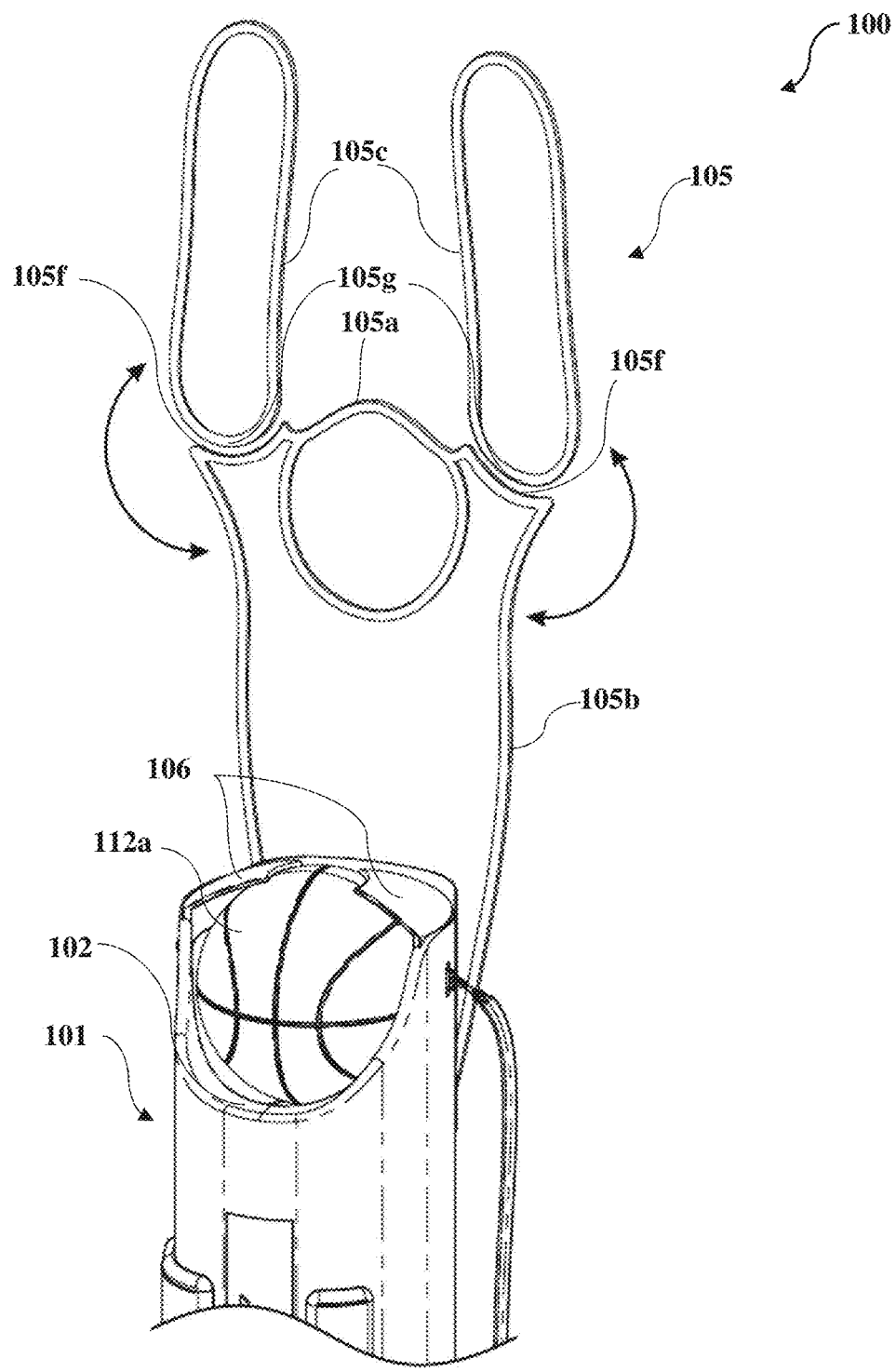
FIG. 16A exemplarily illustrates a partial, front perspective view of an embodiment of the portable sports rack and delivery system, showing the training component comprising movable arms for assisting in training a sportsperson.

FIG. 16A exemplarily illustrates a partial, front perspective view of an embodiment of the portable sports rack and delivery system 100, showing the training component 105 comprising movable arms 105c for assisting in training a sportsperson. The training component 105 is configured as a humanoid shape comprising a head 105a, a body 105b, and arms 105c as disclosed in the description of FIG. 3. In an embodiment, each of the arms 105c of the training component 105 is rotatably connected about a joint 105f, 105g using a motorized control unit 144 exemplarily illustrated in FIGS. 16B-16D. The joint edges 105*f* and 105*g* of each arm 105*c* are opposingly curved to allow rotation against each other in directions indicated by arrows in FIG. 16A, thereby allowing the arms 105*c* to move in lateral directions above the body 105*b* of the training component 105 and provide an obstruction to a basketball 112*a* thrown by a sportsperson, for example, a basketball player, to assist in training the sportsperson.

Figure 16B:
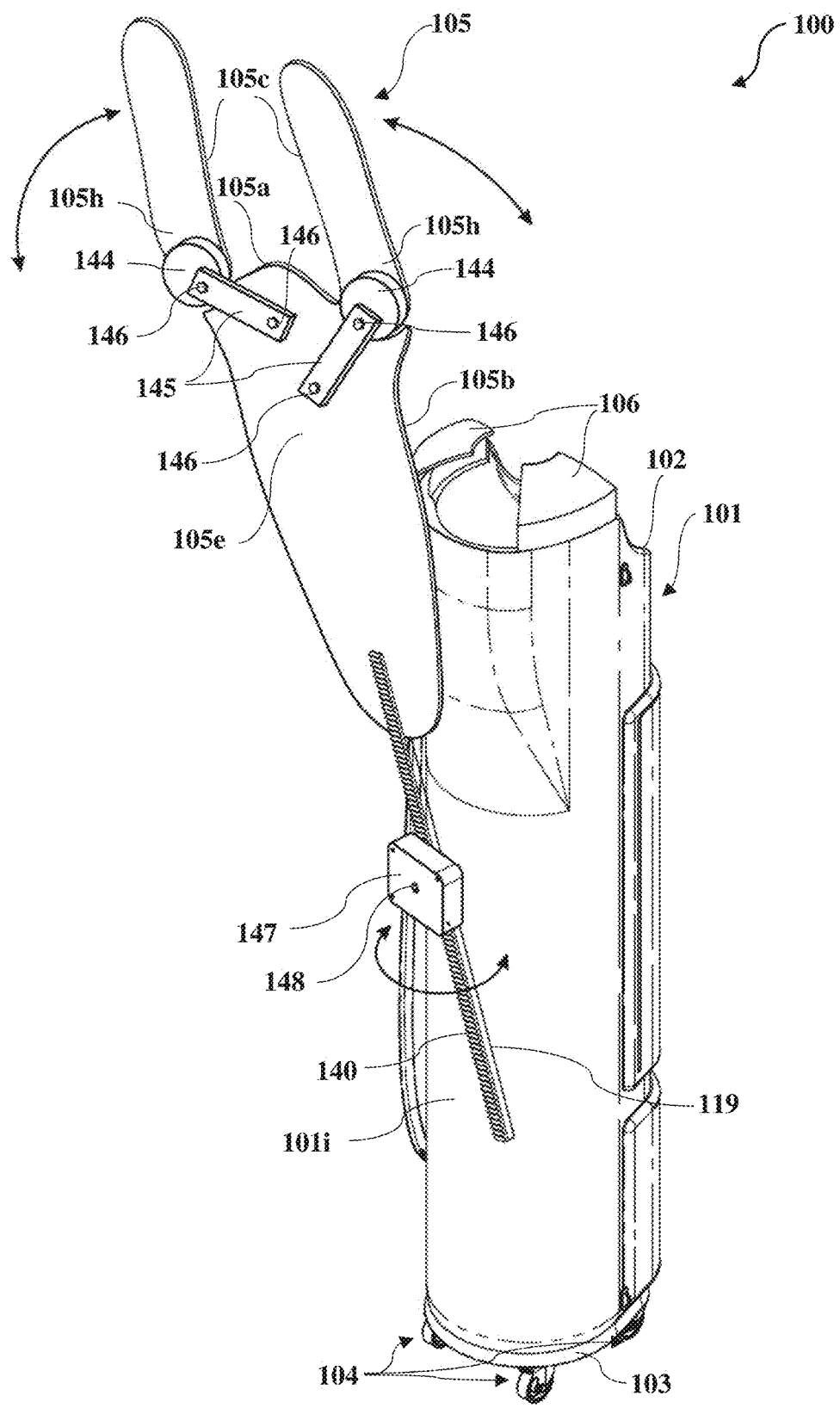
FIGS. 16B-16D exemplarily illustrate rear perspective views of an embodiment of the portable sports rack and delivery system, showing movements of the training component in different directions for assisting in training a sportsperson.
Figure 16C:
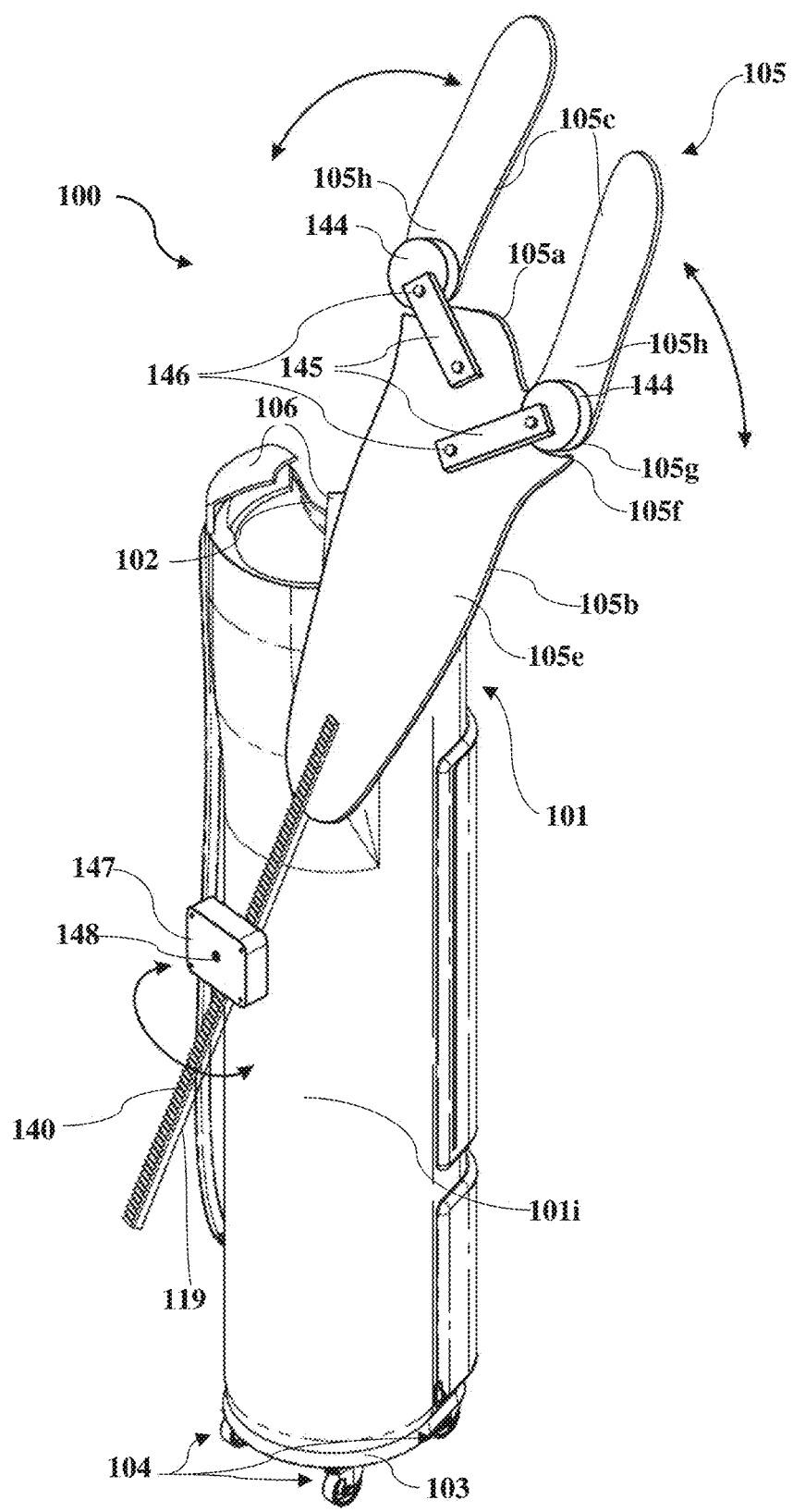
Figure 16D:
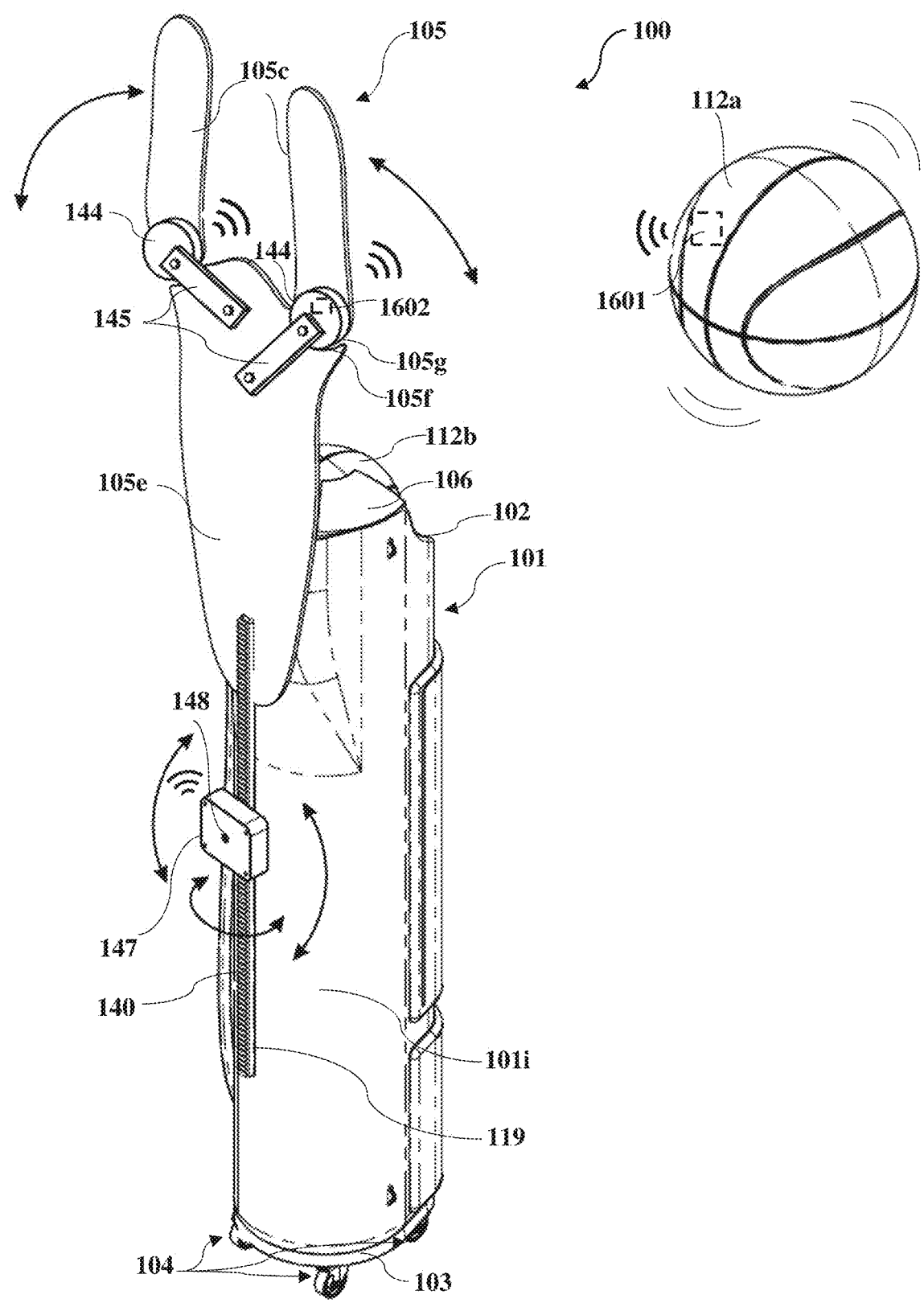

FIGS. 16B-16D exemplarily illustrate rear perspective views of an embodiment of the portable sports rack and delivery system 100, showing movements of the training component 105 in different directions for assisting in training a sportsperson. As disclosed in the description of FIG. 16A, a motorized control unit 144 is used for rotatably connecting each of the arms 105*c* of the training component 105 about the joint 105*f*, 105*g*. In an embodiment, the motorized control units 144 are positioned on rear surfaces 105*h* of the arms 105*c*, proximal to the joint edges 105*g* of the arms 105*c*, and fastened to the rear surface 105*e* of the body 105*b* of the training component 105 using support members 145 and fasteners 146, for example, bolts, as exemplarily illustrated in FIGS. 16B-16D. The motorized control unit 144, when activated, is configured to rotate the arms 105*c* of the training component 105 to simulate an obstruction to a trajectory of a basketball 112*a*, 112*b*, 112*c*, 112*d*, or 112*e* thrown by a sportsperson, for example, a basketball player, to assist in training the sportsperson. In an embodiment, each motorized control unit 144 comprises a motor (not shown), which when activated, rotates each of the arms 105*c* of the training component 105 about the joint 105*f*, 105*g* to move the arms 105*c* in lateral directions indicated by arrows in FIGS. 16B-16D, similar to arm movements made by a defender in a basketball game.

In addition to movements of the arms 105*c* of the training component 105 in lateral directions, in an embodiment, the training component 105 is configured to move about a pivot 148 in lateral directions as indicated by arrows in FIGS. 16B-16C. In this embodiment, a training control unit 147 is operably coupled to the support member 119 of the training component 105 and attached to the rear section 101*i* of the elongate rack enclosure 101 of the portable sports rack and delivery system 100. The training control unit 147 comprises a motor (not shown) and a gear system (not shown) operably coupled to the support member 119 of the training component 105. The training control unit 147 defines a pivot 148 for movement of the training component 105 thereabout in lateral directions similar to a pendulum as indicated by arrows in FIGS. 16B-16C. When the motor in the training control unit 147 is powered on, for example, by a control button (not shown), the internal gear system engages with a rack 140 configured on the support member 119 of the training component 105 and moves the support member 119, and in turn, the training component 105 in lateral directions, for example, a right-hand direction and a left-hand direction, as exemplarily illustrated in FIGS. 16B-16C. The tilting movement of the training component 105 in lateral directions about the pivot 148 simulates an obstruction to a trajectory of a basketball 112*a* thrown by a sportsperson, for example, a basketball player, to assist in training the sportsperson.

In a prophetic embodiment, the motorized control units 144 positioned on the arms 105*c* of the training component 105 comprise motion sensors (not shown) configured to detect movement within a predefined distance of the portable sports rack and delivery system 100. On detecting motion, for example, movement of a basketball or a basketball player, within the predefined distance, the motion sensors activate the motors in their respective motorized control units 144 to move the arms 105*c* of the training component 105 in lateral directions, thereby simulating an obstruction to a trajectory of a basketball 112*a* thrown by the sportsperson to assist in training the sportsperson. In another embodiment, when the motion sensors detect motion within the predefined distance, the motion sensors transmit a signal to the training control unit 147 and activate the motor in the training control unit 147 to move the support member 119, and in turn, the training component 105 in lateral directions, for example, a right-hand direction and a left-hand direction, as exemplarily illustrated in FIGS. 16B-16D. In another embodiment, when the motion sensors detect motion within the predefined distance, the motion sensors transmit a signal to a training control unit similar to the training control unit 142 exemplarily illustrated in FIGS. 15A-15C, and activate a motor in the training control unit to move the support member 119, and in turn, the training component 105 in an upward direction and a downward direction as disclosed in the description of FIGS. 15A-15C. In another prophetic embodiment, the motorized control units 144 and the training control unit 147 are activated simultaneously, thereby moving the training component 105 in lateral directions, while simultaneously moving the arms 105*c* of the training component 105 in lateral directions to simulate an obstruction to a trajectory of a basketball 112*a* thrown by the sportsperson to assist in training the sportsperson.

In another prophetic embodiment, a beacon device 1601 exemplarily illustrated in FIG. 16D, is installed in each of the basketballs 112*a*, 112*b*, 112*c*, 112*d*, and 112*e* stored in the storage space 101*g* of the elongate rack enclosure 101. The beacon device 1601 is configured to transmit a signal to the motorized control units 144 exemplarily illustrated in FIG. 16D, to indicate a location of the basketball, for example, 112*a*, being played. The motorized control units 144 are in operable communication, for example, wireless communication, with each beacon device 1601. Each of the motorized control units 144 comprises a receiver module 1602 configured to receive the signal transmitted by each beacon device 1601. On receiving the signal from the beacon device 1601, the motorized control units 144 move the arms 105*c* of the training component 105 in a particular direction in accordance with the signal to counter and obstruct the basketball 112*a* being thrown, thereby assisting in training the sportsperson. In another prophetic embodiment, a mobile application (not shown) is provided for configuring a training plan or a pattern of movement for the training component 105. The mobile application is deployed on a mobile device (not shown), for example, a smartphone, of a user, for example, a coach or a trainer. The motorized control units 144 and the training control unit 147 are programmed to operate in accordance with the training plan or the pattern of movement configured by the mobile application.

Figure 17A:
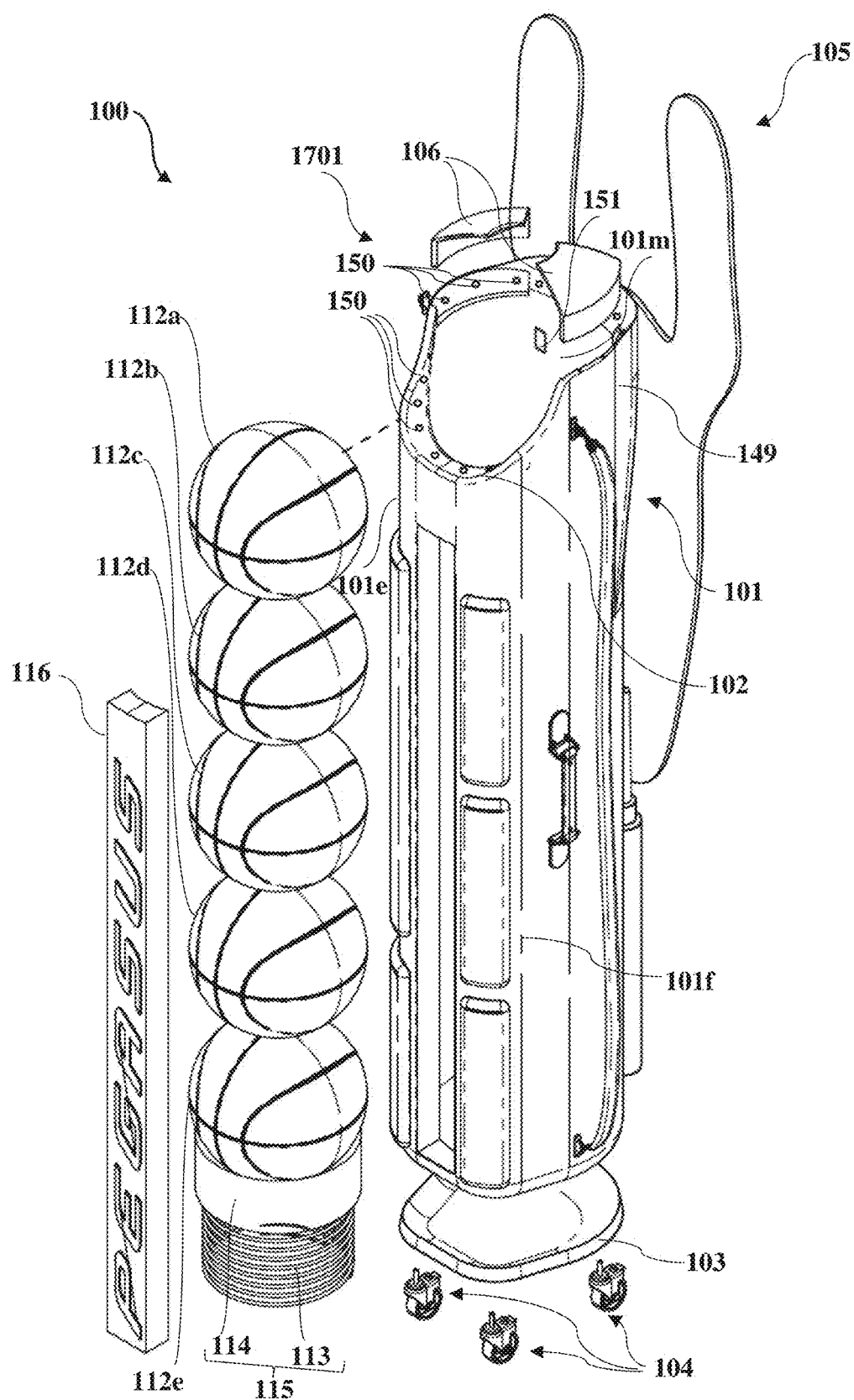
FIGS. 17A-17B exemplarily illustrate front perspective, exploded views of an embodiment of the portable sports rack and delivery system, showing an implementation of a sanitizing system operably coupled to the elongate rack enclosure.
Figure 17B:
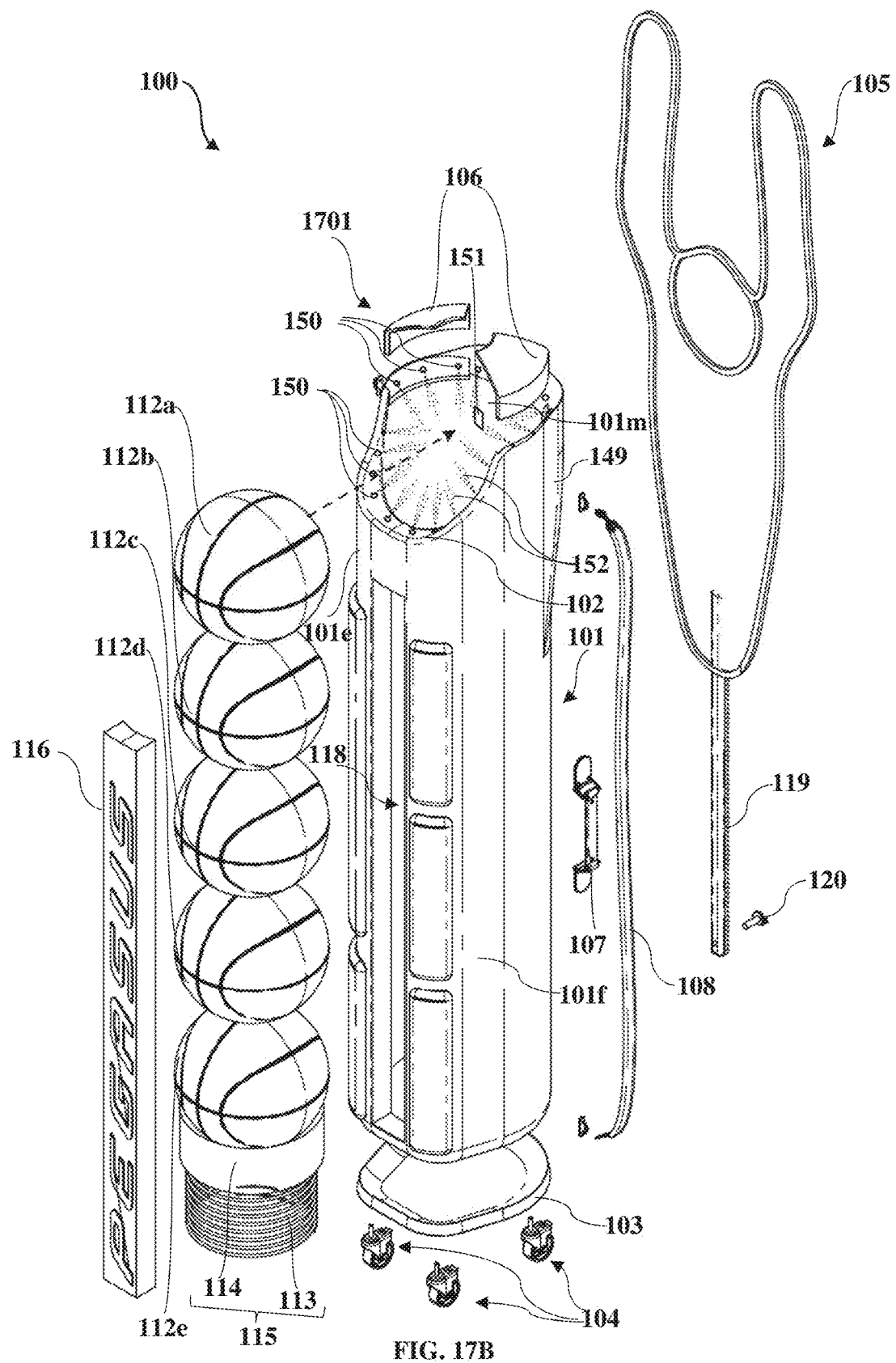

FIGS. 17A-17B exemplarily illustrate front perspective, exploded views of an embodiment of the portable sports rack and delivery system 100, showing an implementation of a sanitizing system 1701 operably coupled to the elongate rack enclosure 101. In this embodiment, the sanitizing system 1701 comprises a reservoir 149 and multiple nozzles 150. The reservoir 149 is positioned in the rear section 101*i* of the elongate rack enclosure 101. The reservoir 149 is configured to contain a sanitizing solution 152 for sanitizing one or more of the stacked balls, for example, the stacked basketballs 112*a*, 112*b*, 112*c*, 112*d*, and 112*e*, in the storage space 101*g* of the elongate rack enclosure 101. The nozzles 150 are operably coupled to the reservoir 149 and positioned at predetermined locations on the elongate rack enclosure 101. For example, the nozzles 150 are positioned peripherally along the delivery opening 102 as exemplarily illustrated in FIGS. 17A-17B. The nozzles 150 are, for example, spray nozzles, configured to spray the sanitizing solution 152 contained in the reservoir 149. When activated, the nozzles 150, in fluid communication with the reservoir 149, are configured to dispense the sanitizing solution 152 on one or more of the stacked basketballs 112*a*, 112*b*, 112*c*, 112*d*, and 112*e* in the storage space 101*g* of the elongate rack enclosure 101. For example, when activated, the nozzles 150, in fluid communication with the reservoir 149, dispense the sanitizing solution 152 on the uppermost basketball 112*a* positioned at the delivery opening 102. In another prophetic embodiment (not shown), the nozzles 150 are positioned internally along the length or the sides 101*e* and 101*f* of the elongate rack enclosure 101 for dispensing the sanitizing solution 152 from the reservoir 149 to all the stacked basketballs 112*a*, 112*b*, 112*c*, 112*d*, and 112*e* in the storage space 101*g* of the elongate rack enclosure 101. In another prophetic embodiment (not shown), the nozzles 150 are positioned internally along the walls 101*j* and 101*k* of the elongate rack enclosure 101 exemplarily illustrated in FIG. 7B, for dispensing the sanitizing solution 152 from the reservoir 149 to all the stacked basketballs 112*a*, 112*b*, 112*c*, 112*d*, and 112*e* in the storage space 101*g* of the elongate rack enclosure 101.

In an embodiment as exemplarily illustrated in FIGS. 17A-17B, a control element 151, for example, a button or a sensor, is operably coupled to the reservoir 149 and the nozzles 150 for activating the nozzles 150 and dispensing the sanitizing solution 152 from the reservoir 149 to the uppermost basketball 112*a* via the nozzles 150. The control element 151 is positioned on an inner surface 101*m* of the elongate rack enclosure 101 as exemplarily illustrated in FIGS. 17A-17B. In another prophetic embodiment, a sensor (not shown) is positioned proximal to the delivery opening 102 to detect the presence of the uppermost basketball 112*a* at the delivery opening 102. In this embodiment, on detecting the presence of the uppermost basketball 112*a* at the delivery opening 102, the sensor transmits a signal to activate the nozzles 150 and dispense the sanitizing solution 152 from the reservoir 149 to the uppermost basketball 112*a*. The sanitizing system 1701 is configured to spray the sanitizing solution 152 on the uppermost basketball 112*a* when the basketball 112*a* is inserted into or removed from the storage space 101*g* of the elongate rack enclosure 101.

Figure 17C:
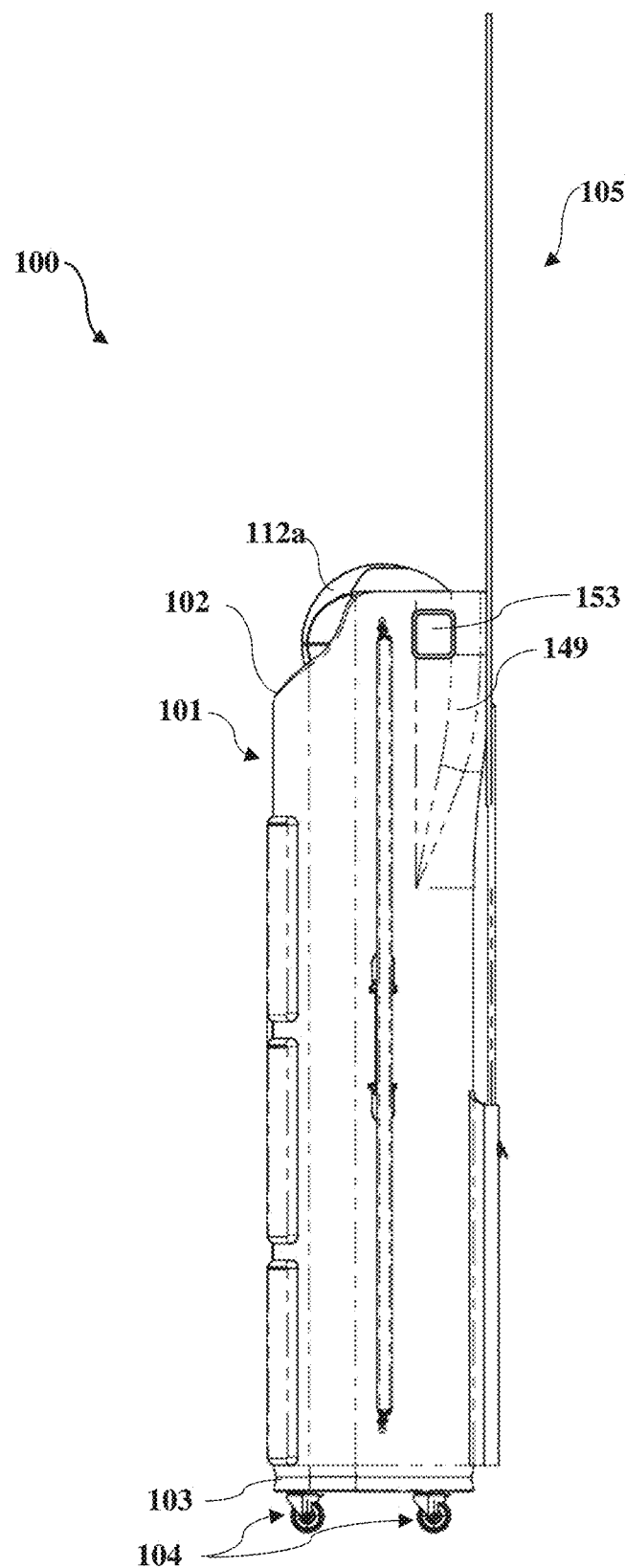
FIG. 17C exemplarily illustrates a side elevation view of an embodiment of the portable sports rack and delivery system, showing a position of a reservoir of the sanitizing system.

FIG. 17C exemplarily illustrates a side elevation view of an embodiment of the portable sports rack and delivery system 100, showing a position of the reservoir 149 of the sanitizing system 1701. As exemplarily illustrated in FIG. 17C, the reservoir 149 is positioned in the rear section 101*i* of the elongate rack enclosure 101. In an embodiment, the reservoir 149 comprises a side door 153 that closes an opening (not shown) of the reservoir 149. The side door 153 is opened to refill the sanitizing solution 152 in the reservoir 149 for dispensing the sanitizing solution 152 through the nozzles 150 as exemplarily illustrated in FIG. 17B.

Figure 18:
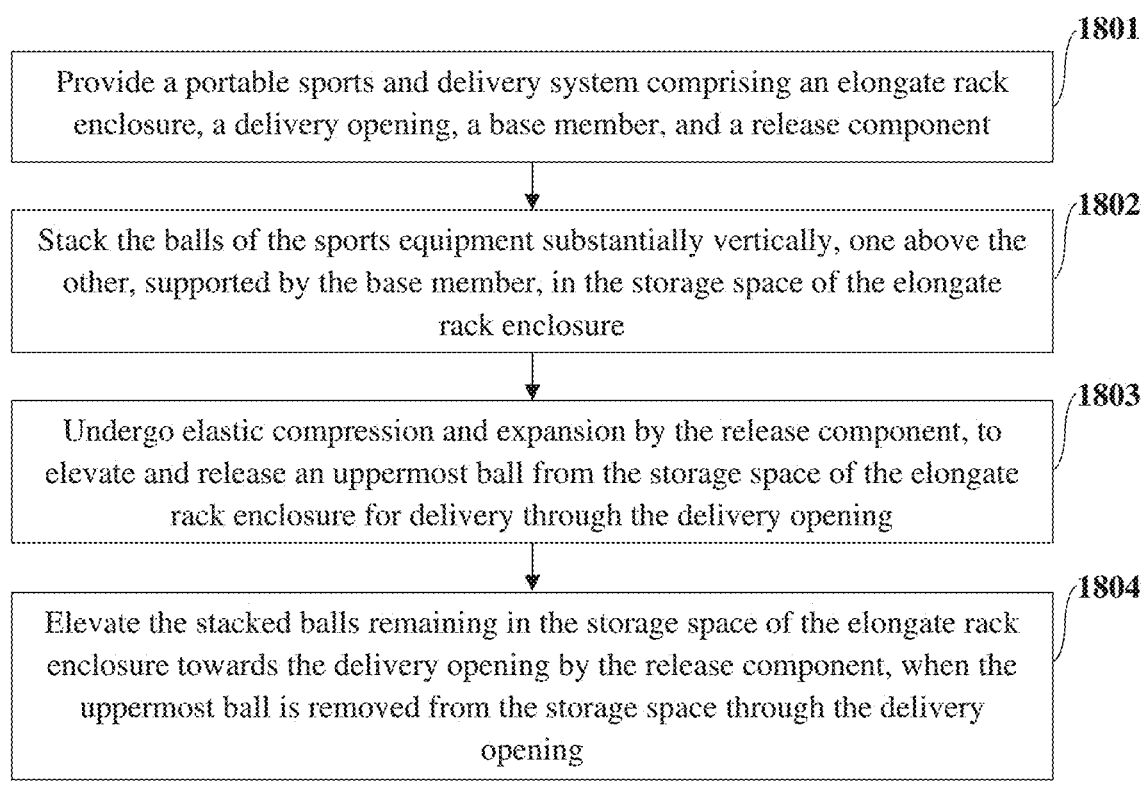
FIG. 18 illustrates a flowchart of an embodiment of a method for storing and delivering sports equipment using the portable sports rack and delivery system.

FIG. 18 illustrates a flowchart of an embodiment of a method for storing and delivering sports equipment using the portable sports rack and delivery system 100. In the method disclosed herein, the portable sports rack and delivery system 100 comprising the elongate rack enclosure 101 with the delivery opening 102, the base member 103, and the release component 115 as exemplarily illustrated in FIG. 1, FIGS. 2A-2B, FIGS. 6A-6B, FIGS. 7A-7C, FIGS. 8-10, and FIGS. 11A-11B and as disclosed in the description thereof, is provided 1801. Ball-shaped sports equipment or balls, for example, basketballs, are stacked 1802 substantially vertically, one above the other, supported by the base member 103, in the storage space 101*g* of the elongate rack enclosure 101. During operation of the portable sports rack and delivery system 100, the release component 115 undergoes 1803 elastic compression and expansion to elevate and release an uppermost ball from the storage space 101*g* of the elongate rack enclosure 101 for delivery through the delivery opening 102. When the uppermost ball is removed from the storage space 101*g* through the delivery opening 102, the release component 115 elevates 1804 the stacked balls remaining in the storage space 101; of the elongate rack enclosure 101 towards the delivery opening 102.

In an embodiment, the method disclosed herein also facilitates training of a sportsperson, for example, a basketball player, a football player, etc., using the training component 105 exemplarily illustrated in FIGS. 1-3. In an embodiment, the arms 105*c* of the training component 105 are rigidly connected to the body 105*b* of the training component 105 as exemplarily illustrated in FIGS. 1-3. In this embodiment, the arms 105*c* are in a raised position at all times to simulate an obstruction to a trajectory of a ball thrown by a sportsperson. In another embodiment, the arms 105*c* of the training component 105 are rotatably connected to the body 105*b* of the training component 105 as exemplarily illustrated in FIGS. 16A-16D. In this embodiment, the movement of the arms 105*c* are similar to the arm movements made by a defender in a sports game, for example, a basketball game, thereby allowing simulation of a real-time game situation. The height of the training component 105 is configured to be adjusted by sliding the support member 119 of the training component 105 exemplarily illustrated in FIGS. 2A-3 and FIGS. 7B-7C, in an upward position or a downward position and securing the support member 119 to the rear section 101*i* of the elongate rack enclosure 101 at a required height as disclosed in the description of FIG. 7C. For example, a user, for example, a coach or a basketball player, inserts the lower end 119*b* of the support member 119 into the holding space 125 of the holder 122 and secures the opening 119*c* at the lower end 119*b* of the support member 119 to one of the openings 124 of the holder 122 using the lock pin 120 as exemplarily illustrated in FIG. 7C. The training component 105 is lowered or raised by sliding the support member 119 in and out of the holder 122, and thereafter securing the lower end 119*b* of the support member 119 at a required height by inserting the lock pin 120 through the opening 119*c* at the lower end 119*b* of the support member 119 and through one of the openings 124 of the holder 122. In another example, the training component 105 is adjustably coupled to the rear section 101*i* of the elongate rack enclosure 101 using the telescopic assembly 1201 exemplarily illustrated in FIGS. 12A-12B. The training component 105 extends above the upper end 101*a* of the elongate rack enclosure 101 to assist in training the sportsperson as disclosed in the description of FIG. 3.

The portable sports rack and delivery system 100 is convenient and easy to use by sportspersons, for example, basketball coaches at all levels such as beginner, intermediate, and professional level basketball coaches; basketball players at all levels such as beginner, intermediate, and professional level basketball players; basketball trainers at all levels; at clinics and camps at all levels; by school and professional basketball teams of all levels; and by persons at residential homes.

The foregoing examples and illustrative implementations of various embodiments have been provided merely for explanation and are in no way to be construed as limiting of the embodiments disclosed herein. Dimensions of various parts of the portable sports rack and delivery system disclosed above are exemplary, and are not limiting of the scope of the embodiments herein. While the embodiments have been described with reference to various illustrative implementations, drawings, and techniques, it is understood that the words, which have been used herein, are words of description and illustration, rather than words of limitation. Furthermore, although the embodiments have been described herein with reference to particular means, materials, techniques, and implementations, the embodiments herein are not intended to be limited to the particulars disclosed herein; rather, the embodiments extend to all functionally equivalent structures, methods and uses, such as are within the scope of the appended claims. It will be understood by those skilled in the art, having the benefit of the teachings of this specification, that the embodiments disclosed herein are capable of modifications and other embodiments may be effected and changes may be made thereto, without departing from the scope and spirit of the embodiments disclosed herein.

I claim:

1. A portable sports rack and delivery system comprising:
   an elongate rack enclosure defining a storage space extending from a first end to a second end of the elongate rack enclosure, the storage space configured to accommodate sports equipment, wherein the sports equipment comprises balls stacked substantially vertically, one above the other, and disposed in the storage space;
   a delivery opening disposed at the first end of the elongate rack enclosure, wherein the delivery opening is configured to receive, accommodate, and deliver an uppermost one of the stacked balls from the storage space of the elongate rack enclosure;
   a base member attached to the second end of the elongate rack enclosure, wherein the base member is configured to support the stacked balls within the storage space of the elongate rack enclosure;
   a release component disposed on an upper surface of the base member within the storage space of the elongate rack enclosure, wherein the release component is configured to elastically compress and expand to elevate and release the uppermost one of the balls from the storage space of the elongate rack enclosure for delivery through the delivery opening;
   a training component operably and adjustably coupled to a rear section of the elongate rack enclosure, wherein the training component is configured to extend above the first end of the elongate rack enclosure to assist in training a sportsperson, and wherein the training component comprises:
      a frame configured in a humanoid shape with a head, a body, and arms extending from the body, and wherein the arms are configured in a raised position to simulate an obstruction to a trajectory of a ball thrown by the sportsperson to assist in the training of the sportsperson; and
      a mesh configured to cover spaces defined by the frame for optimally obstructing the ball thrown by the sportsperson to assist in training the sportsperson.

2. The portable sports rack and delivery system of claim 1, wherein the elongate rack enclosure is of a generally cylindrical shape and is configured to stand in a substantially vertical position, and wherein the balls are stored in a substantially vertical orientation within the storage space of the elongate rack enclosure.

3. The portable sports rack and delivery system of claim 1, wherein the release component comprises a compression spring and a spring base, wherein a first end of the compression spring is operably coupled to the base member, and wherein a second end of the compression spring is operably coupled to the spring base, and wherein the spring base, in operable communication with the compression spring, is configured to elevate the stacked balls remaining in the storage space of the elongate rack enclosure towards the delivery opening when the uppermost one of the stacked balls is removed from the storage space through the delivery opening.

4. The portable sports rack and delivery system of claim 1, further comprising a holder attached to the rear section of the elongate rack enclosure, wherein the holder comprises a holding space and openings spaced at predetermined intervals thereon, and wherein the holder is configured to accommodate and secure a support member of the training component in the holding space at a required height by inserting a fastener through an opening of the support member and through one of the openings of the holder, and wherein height of the training component is adjusted by sliding the support member in the holding space of the holder in one of an upward position and a downward position and securing the support member to the one of the openings of the holder at the required height using the fastener.

5. The portable sports rack and delivery system of claim 1, wherein the training component is adjustably coupled to the rear section of the elongate rack enclosure using a telescopic assembly.

6. The portable sports rack and delivery system of claim 1, further comprising one or more stopper elements operably attached to the first end of the elongate rack enclosure, wherein the one or more stopper elements are configured to one of partially and fully cover the delivery opening and contain the uppermost one of the balls within the storage space of the elongate rack enclosure.

7. The portable sports rack and delivery system of claim 1, further comprising wheel assemblies operably coupled to a bottom surface of the base member, wherein the wheel assemblies are configured to transport the portable sports rack and delivery system.

8. The portable sports rack and delivery system of claim 7, further comprising a locking member operably coupled to each of at least two of the wheel assemblies, wherein the locking member is configured to lock the each of the at least two of the wheel assemblies and brake movement of the portable sports rack and delivery system.

9. The portable sports rack and delivery system of claim 1, further comprising a plate member attached to a bottom surface of the base member, wherein the plate member is configured to stabilize the elongate rack enclosure and preclude the elongate rack enclosure from tipping when the elongate rack enclosure is in a substantially vertical position.

10. The portable sports rack and delivery system of claim 1, further comprising one or more handle elements attached to an outer surface of the elongate rack enclosure, wherein the one or more handle elements are configured to allow gripping and carrying of the portable sports rack and delivery system in one of a substantially horizontal position and a substantially vertical position.

11. The portable sports rack and delivery system of claim 1, further comprising an elongate opening disposed at a front section of the elongate rack enclosure, wherein the elongate opening is configured to accommodate a display structure on the elongate rack enclosure.

12. The portable sports rack and delivery system of claim 1, further comprising a plurality of pockets of same and/or different shapes and sizes positioned at predetermined locations on an outer surface of the elongate rack enclosure, wherein the pockets are configured to store items and accessories of the sports equipment.

13. The portable sports rack and delivery system of claim 1, further comprising a delivery system operably coupled to the release component, wherein the delivery system comprises:
   a guide element defining a channel extending along a length of the elongate rack enclosure; and
   a lever comprising a first end and a second end, wherein the first end of the lever is connected to the release component, and wherein the second end of the lever extends outwardly from the channel of the guide element, and wherein the lever is configured to traverse the channel of the guide element and move the release component in an upward direction from the second end of the elongate rack enclosure towards the delivery opening at the first end of the elongate rack enclosure for delivering the uppermost one of the stacked balls from the storage space of the elongate rack enclosure.

14. The portable sports rack and delivery system of claim 13, further comprising a locking member attached to an end of the guide element proximal to the second end of the elongate rack enclosure, wherein the locking member is configured to lock the lever, and in turn, the release component, in position at the end of the guide element.

15. The portable sports rack and delivery system of claim 1, wherein the balls are selected from the group consisting of basketballs, footballs, soccer balls, volleyballs, beachballs, and handballs.

16. A portable sports rack and delivery system comprising:
   an elongate rack enclosure defining a storage space extending from a first end to a second end of the elongate rack enclosure, the storage space configured to accommodate sports equipment, wherein the sports equipment comprises balls stacked substantially vertically, one above the other, and disposed in the storage space;
   a delivery opening disposed at the first end of the elongate rack enclosure, wherein the delivery opening is configured to receive, accommodate, and deliver an uppermost one of the stacked balls from the storage space of the elongate rack enclosure;
   a base member attached to the second end of the elongate rack enclosure, wherein the base member is configured to support the stacked balls within the storage space of the elongate rack enclosure;
   a release component disposed on an upper surface of the base member within the storage space of the elongate rack enclosure, wherein the release component is configured to elastically compress and expand to elevate and release the uppermost one of the balls from the storage space of the elongate rack enclosure for delivery through the delivery opening;
   a training component operably and adjustably coupled to a rear section of the elongate rack enclosure, wherein the training component is configured to extend above the first end of the elongate rack enclosure to assist in training a sportsperson, wherein the training component comprises:
      a frame configured in a humanoid shape with a head, a body, and arms extending from the body, wherein the arms are configured in a raised position to simulate an obstruction to a trajectory of a ball thrown by the sportsperson to assist in training the sportsperson, wherein each of the arms is rotatably connected about a joint using a motorized control unit, wherein the motorized control unit, when activated, is configured to rotate the arms of the training component and simulate an obstruction to the trajectory of the ball thrown by the sportsperson to assist in the training of the sportsperson.

17. A portable sports rack and delivery system comprising:
   an elongate rack enclosure defining a storage space extending from a first end to a second end of the elongate rack enclosure, the storage space configured to accommodate sports equipment, wherein the sports equipment comprises balls stacked substantially vertically, one above the other, and disposed in the storage space;
   a delivery opening disposed at the first end of the elongate rack enclosure, wherein the delivery opening is configured to receive, accommodate, and deliver an uppermost one of the stacked balls from the storage space of the elongate rack enclosure;
   a base member attached to the second end of the elongate rack enclosure, wherein the base member is configured to support the stacked balls within the storage space of the elongate rack enclosure;
   a release component disposed on an upper surface of the base member within the storage space of the elongate rack enclosure, wherein the release component is configured to elastically compress and expand to elevate and release the uppermost one of the balls from the storage space of the elongate rack enclosure for delivery through the delivery opening;
   a training component operably and adjustably coupled to a rear section of the elongate rack enclosure, wherein the training component is configured to extend above the first end of the elongate rack enclosure to assist in training a sportsperson; and
   a gear system operably coupled to and in engageable communication with a support member of the training component at the rear section of the elongate rack enclosure, wherein the gear system, when activated, is configured to move the training component in one of an upward direction, a downward direction, and lateral directions to simulate an obstruction to a trajectory of a ball thrown by the sportsperson to assist in the training of the sportsperson.

18. A portable sports rack and delivery system comprising:
   an elongate rack enclosure defining a storage space extending from a first end to a second end of the elongate rack enclosure, the storage space configured to accommodate sports equipment, wherein the sports equipment comprises balls stacked substantially vertically, one above the other, and disposed in the storage space;
   a delivery opening disposed at the first end of the elongate rack enclosure, wherein the delivery opening is configured to receive, accommodate, and deliver an uppermost one of the stacked balls from the storage space of the elongate rack enclosure;
   a base member attached to the second end of the elongate rack enclosure, wherein the base member is configured to support the stacked balls within the storage space of the elongate rack enclosure;
a release component disposed on an upper surface of the base member within the storage space of the elongate rack enclosure, wherein the release component is configured to elastically compress and expand to elevate and release the uppermost one of the balls from the storage space of the elongate rack enclosure for delivery through the delivery opening;
a training component operably and adjustably coupled to a rear section of the elongate rack enclosure, wherein the training component is configured to extend above the first end of the elongate rack enclosure to assist in training a sportsperson; and
a sanitizing system operably coupled to the elongate rack enclosure, the sanitizing system comprising:
 a reservoir positioned in the rear section of the elongate rack enclosure, wherein the reservoir is configured to contain a sanitizing solution for sanitizing one or more of the stacked balls in the storage space of the elongate rack enclosure; and
 a plurality of nozzles operably coupled to the reservoir and positioned at predetermined locations on the elongate rack enclosure, wherein, when activated, the nozzles, in fluid communication with the reservoir, are configured to dispense the sanitizing solution on one or more of the stacked balls in the storage space of the elongate rack enclosure.

19. A portable sports rack and delivery system comprising:
an elongate rack enclosure defining a storage space extending from a first end to a second end of the elongate rack enclosure, the storage space configured to accommodate sports equipment, wherein the sports equipment comprises balls stacked substantially vertically, one above the other, and disposed in the storage space;
a delivery opening disposed at the first end of the elongate rack enclosure, wherein the delivery opening is defined by two semicircles in perpendicular relation to each other, wherein a first semicircle is disposed in a horizontal direction at an upper end of the elongate rack enclosure, wherein a second semicircle is disposed in a vertical direction, perpendicular to the direction of the first semicircle, wherein the two semicircles of the delivery opening are configured to receive, accommodate, and deliver an uppermost one of the stacked balls from the storage space of the elongate rack enclosure;
a base member attached to the second end of the elongate rack enclosure, wherein the base member is configured to support the stacked balls within the storage space of the elongate rack enclosure;
a release component disposed on an upper surface of the base member within the storage space of the elongate rack enclosure, wherein the release component is configured to elastically compress and expand to elevate and release the uppermost one of the balls from the storage space of the elongate rack enclosure for delivery through the delivery opening;
a training component operably and adjustably coupled to a rear section of the elongate rack enclosure, wherein the training component is configured to extend above the first end of the elongate rack enclosure to assist in training a sportsperson, wherein the training component comprises:
 a frame configured in a humanoid shape with a head, a body, and arms extending from the body, and wherein the arms are configured in a raised position to simulate an obstruction to a trajectory of a ball thrown by the sportsperson to assist in the training of the sportsperson.

* * * * *